US009780409B2

(12) United States Patent
Takiguchi et al.

(10) Patent No.: US 9,780,409 B2
(45) Date of Patent: Oct. 3, 2017

(54) NONAQUEOUS ELECTROLYTIC SOLUTION AND NONAQUEOUS-ELECTROLYTE BATTERY EMPLOYING THE SAME

(71) Applicant: MITSUBISHI CHEMICAL CORPORATION, Tokyo (JP)

(72) Inventors: Kanako Takiguchi, Ibaraki (JP); Masamichi Onuki, Kanagawa (JP); Minoru Kotato, Ibaraki (JP); Ryo Yamaguchi, Kanagawa (JP); Takeshi Nakamura, Kanagawa (JP); Takayuki Aoshima, Kanagawa (JP)

(73) Assignee: MITSUBISHI CHEMICAL CORPORATION, Tokyo (JP)

( * ) Notice: Subject to any disclaimer, the term of this patent is extended or adjusted under 35 U.S.C. 154(b) by 383 days.

(21) Appl. No.: 14/502,343

(22) Filed: Sep. 30, 2014

(65) Prior Publication Data
US 2015/0024284 A1 Jan. 22, 2015

Related U.S. Application Data

(63) Continuation of application No. PCT/JP2013/059403, filed on Mar. 28, 2013.

(30) Foreign Application Priority Data

Mar. 30, 2012 (JP) ................................. 2012-082142
Oct. 26, 2012 (JP) ................................. 2012-236679

(51) Int. Cl.
*H01M 10/05* (2010.01)
*H01M 10/0567* (2010.01)
*H01M 10/0525* (2010.01)
*C07C 69/96* (2006.01)

(52) U.S. Cl.
CPC ......... *H01M 10/0567* (2013.01); *C07C 69/96* (2013.01); *H01M 10/0525* (2013.01); *H01M 2300/0025* (2013.01); *H01M 2300/0028* (2013.01); *H01M 2300/0034* (2013.01)

(58) Field of Classification Search
CPC .... H01M 4/58; H01M 4/587; H01M 10/0525; H01M 10/0567; C07C 69/96
See application file for complete search history.

(56) References Cited

U.S. PATENT DOCUMENTS

| | | | |
|---|---|---|---|
| 4,530,747 A | 7/1985 | Doenges et al. | |
| 5,776,627 A | 7/1998 | Mao et al. | |
| 5,879,834 A | 3/1999 | Mao | |
| 6,033,797 A | 3/2000 | Mao et al. | |
| 6,074,777 A | 6/2000 | Reimers et al. | |
| 6,632,572 B1 | 10/2003 | Yasutake et al. | |
| 2002/0122988 A1 | 9/2002 | Hamamoto et al. | |
| 2002/0197537 A1 | 12/2002 | Kim et al. | |
| 2005/0142448 A1 | 6/2005 | Kim et al. | |
| 2005/0244719 A1 | 11/2005 | Kim et al. | |
| 2008/0014496 A1 | 1/2008 | Watanabe et al. | |
| 2010/0035146 A1 | 2/2010 | Fujii et al. | |
| 2010/0227227 A1 | 9/2010 | Kim et al. | |
| 2011/0123871 A1 | 5/2011 | Nakagawa et al. | |
| 2011/0183199 A1 | 7/2011 | Abe | |
| 2011/0229808 A1 | 9/2011 | Yu et al. | |
| 2012/0219854 A1 | 8/2012 | Nakagawa et al. | |
| 2012/0231330 A1 | 9/2012 | Fujii et al. | |
| 2012/0308883 A1 | 12/2012 | Nakagawa et al. | |
| 2013/0337318 A1 | 12/2013 | Fujii et al. | |
| 2014/0134481 A1 | 5/2014 | Nakagawa et al. | |
| 2015/0162644 A1 | 6/2015 | Fujii et al. | |

FOREIGN PATENT DOCUMENTS

| | | |
|---|---|---|
| CN | 1285622 A | 2/2001 |
| CN | 1385919 A | 12/2002 |
| CN | 101960662 A | 1/2011 |
| CN | 102099956 A | 6/2011 |
| JP | 63-205318 | 8/1988 |
| JP | 07-302614 | 11/1995 |
| JP | 9-106835 | 4/1997 |
| JP | 9-171840 | 6/1997 |
| JP | 11-162512 | 6/1999 |
| JP | 2000-058116 | 2/2000 |
| JP | 2000-058117 | 2/2000 |
| JP | 2000-182663 | 6/2000 |
| JP | 2000-294279 A | 10/2000 |
| JP | 2001-15155 | 1/2001 |
| JP | 2001-043900 | 2/2001 |
| JP | 2001-52735 | 2/2001 |
| JP | 2002-50398 | 2/2002 |

(Continued)

OTHER PUBLICATIONS

Machine Translation of: JP 2001/043900 A, Kolb et al., Feb. 16, 2001.*
Combined Chinese Office Action and Search Report issued Jul. 28, 2016 in Patent Application No. 201380017344.7 (with partial machine English translation and English translation of categories of cited documents).
Japanese Office Action issued Jun. 21, 2016 in Patent Application No. 2012-236679 (with English language translation).
Combined Chinese Office Action and Search Report issued Jan. 26, 2016 in Patent Application No. 201380017344.7 (with English language translation).
Office Action issued Feb. 2, 2016 in Japanese Patent Application No. 2012-082142 (with English language translation).
Office Action issued Jul. 19, 2016 in Japanese Patent Application No. 2012-082142 (with unedited computer generated English language translation).
International Search Report issued May 21, 2013 in PCT/JP2013/059403 filed Mar. 28, 2013.
U.S. Appl. No. 14/582,676, filed Dec. 24, 2014, Takiguchi, et al.

*Primary Examiner* — Kenneth Douyette
(74) *Attorney, Agent, or Firm* — Oblon, McClelland, Maier & Neustadt, L.L.P.

(57) ABSTRACT

The present invention is to provide: a nonaqueous-electrolyte battery excellent in terms of safety during overcharge and high-temperature storability; and a nonaqueous electrolytic solution which gives the battery. The present invention relates to a nonaqueous electrolytic solution comprising an electrolyte and a nonaqueous solvent, wherein the nonaqueous electrolytic solution comprises at least one of specific compounds.

7 Claims, No Drawings

(56) References Cited

FOREIGN PATENT DOCUMENTS

| | | |
|---|---|---|
| JP | 2002-056892 | 2/2002 |
| JP | 2003-109660 | 4/2003 |
| JP | 2003-243026 | 8/2003 |
| JP | 2005-142157 | 6/2005 |
| JP | 3870584 | 10/2006 |
| JP | 4051947 | 12/2007 |
| JP | 2008-166271 A | 7/2008 |
| JP | 2008-251259 | 10/2008 |
| JP | 2009-231283 A | 10/2009 |

* cited by examiner

NONAQUEOUS ELECTROLYTIC SOLUTION AND NONAQUEOUS-ELECTROLYTE BATTERY EMPLOYING THE SAME

TECHNICAL FIELD

The present invention relates to a nonaqueous electrolytic solution and a nonaqueous-electrolyte battery employing the electrolytic solution.

BACKGROUND ART

Nonaqueous-electrolyte batteries including lithium secondary batteries are being put to practical use in extensive applications ranging from power sources for so-called public use, such as portable telephones and notebook type personal computers, to vehicle-mounted power sources for driving motor vehicles or the like. However, recent nonaqueous-electrolyte batteries are increasingly required to have higher performance and, in particular, there is a desire for improvements in various battery characteristics including high capacity, low-temperature use characteristics, high-temperature storability, cycling characteristics, and safety during overcharge.

The electrolytic solutions for use in nonaqueous-electrolyte batteries are usually constituted mainly of an electrolyte and a nonaqueous solvent. Used as main components of the nonaqueous solvent are cyclic carbonates such as ethylene carbonate and propylene carbonate, chain carbonates such as dimethyl carbonate, diethyl carbonate, and ethyl methyl carbonate, and cyclic carboxylic acid esters such as γ-butyrolactone and γ-valerolactone.

Various investigations have been made on nonaqueous solvents, electrolytes, and additives in order to improve the battery characteristics, such as load characteristics, cycling characteristics, and storability, of such nonaqueous-electrolyte batteries or to enhance the safety of the batteries during overcharge. Patent document 1 proposes a technique in which an additive that polymerizes at battery voltages higher than the maximum working voltage of batteries is incorporated into an electrolytic solution to thereby protect the battery by increasing the internal resistance thereof. Patent document 2 proposes a technique in which an additive that polymerizes at battery voltages higher than the maximum working voltage of batteries and that thereby evolves a gas to elevate the pressure is incorporated into an electrolytic solution to thereby enable an internal breaker disposed for protection from overcharge to work without fail. Disclosed as these additives are aromatic compounds such as biphenyl, thiophene, and furan.

Patent document 3 proposes a nonaqueous-electrolyte secondary battery system including both a nonaqueous-electrolyte secondary battery in which phenylcyclohexane has been added to the nonaqueous electrolytic solution in an amount of 0.1-20 parts by weight in order to inhibit the decrease in battery characteristics due to the use of biphenyl or thiophene and a charge control system which senses an increase in battery temperature to break the circuit for charge.

Patent documents 4 to 9 propose techniques in which various aromatics including cyclohexylbenzene are added to electrolytic solutions, and problems concerning improvement in safety during overcharge and durability have been solved to some degree.

Patent document 10 proposes a technique in which in order to enable a nonaqueous-electrolyte secondary battery to combine cycling characteristics and safety during overcharge, 2,2-diphenylpropane or the like is added to the electrolytic solution.

Patent document 11 proposes a technique in which in order to improve the cycling characteristics of a nonaqueous-electrolyte secondary battery, a benzyl alkyl carbonate or a 5-membered or 6-membered lactone containing a phenyl group is incorporated into the nonaqueous electrolytic solution.

Patent document 12 proposes a technique in which in order to reduce gas evolution in a nonaqueous-electrolyte secondary battery during high-temperature storage while maintaining the capacity, an aromatic ester compound or the like is incorporated into the nonaqueous electrolytic solution.

Examples of methods for increasing capacity which are being investigated include: a method in which the active-material layers of electrodes are pressed and densified to thereby minimize the volume within the battery which is occupied by components other than the active materials; and a method in which the range over which a positive electrode is utilized is widened to use the positive electrode up to a higher potential. However, in cases when the active-material layer of an electrode is pressed and densified, it becomes difficult to evenly use the active material and the reactions come to proceed unevenly, resulting in partial deposition of lithium and accelerated deterioration of the active material. It is hence difficult to obtain sufficient properties. Meanwhile, in cases when the range over which a positive electrode is utilized is widened to use the positive electrode up to a higher potential, the positive electrode has further enhanced activity and the deterioration thereof is prone to be accelerated by the reaction between the positive electrode and the electrolytic solution.

Patent document 13 proposes a technique in which in order to enable a nonaqueous-electrolyte secondary battery to combine cycling characteristics and high-temperature storability with safety during overcharge, the diacetate of bisphenol A or the like is incorporated into the nonaqueous electrolytic solution.

PRIOR-ART LITERATURE

Patent Documents

Patent Document 1: JP-A-9-106835
Patent Document 2: JP-A-9-171840
Patent Document 3: JP-A-2002-50398
Patent Document 4: JP-A-2001-15155
Patent Document 5: JP-A-2002-56892
Patent Document 6: JP-A-2003-109660
Patent Document 7: JP-A-7-302614
Patent Document 8: JP-A-2000-58117
Patent Document 9: JP-A-2000-58116
Patent Document 10: JP-A-11-162512
Patent Document 11: Japanese Patent No. 3870584
Patent Document 12: Japanese Patent No. 4051947
Patent Document 13: JP-A-2005-142157

SUMMARY OF THE INVENTION

Problems that the Invention is to Solve

However, nonaqueous-electrolyte secondary batteries employing the electrolytic solutions described in patent documents 1 to 10 suffer decreases in initial capacity and high-temperature storability although showing improved overcharge characteristics, and are still insufficient. Meanwhile, nonaqueous-electrolyte secondary batteries employing the electrolytic solutions described in patent documents 11 to 13 are unsatisfactory in terms of improvement in safety during overcharge.

In view of those problems, an object of the invention is to provide a nonaqueous electrolytic solution which is excellent in terms of safety during overcharge and high-temperature storability and a nonaqueous-electrolyte battery containing the nonaqueous electrolytic solution.

Means for Solving the Problems

The present inventors made various investigations in order to achieve the object. As a result, the inventors have found that those problems can be overcome by incorporating a compound having a specific structure into an electrolytic solution. The invention has been thus completed. Namely, essential points of the invention are as shown below.

<1> A nonaqueous electrolytic solution comprising an electrolyte and a nonaqueous solvent, wherein the nonaqueous electrolytic solution comprises at least one of a compound represented by general formula (I) and a compound represented by general formula (II):

[Chem. 1]

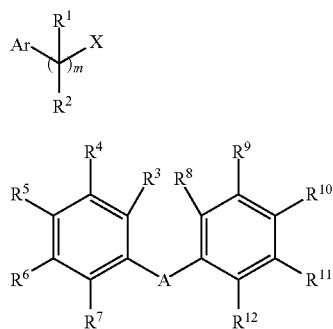

wherein, in general formula (I), Ar represents an aryl group which may have a substituent, m represents an integer of 2 or larger, X represents an alkoxycarbonyloxy group, an organic sulfonate group, or a phosphoric acid ester group, and $R^1$ and $R^2$ each independently represent a hydrogen atom, a halogen atom, or an optionally substituted hydrocarbon group having 1-12 carbon atoms, in the general formula (II), A represents a divalent substituent which may contain a heteroatom, $R^3$ to $R^{12}$ each independently represent a hydrogen atom, a halogen atom, an optionally substituted hydrocarbon group having 1-12 carbon atoms, an alkoxy group, an alkoxycarbonyloxy group, an organic sulfonate group, or a phosphoric acid ester group, and at least one of the $R^3$ to $R^{12}$ representing an alkoxycarbonyloxy group, an organic sulfonate group, or a phosphoric acid ester group.

<2> The nonaqueous electrolytic solution according to the <1> above, wherein Ar in general formula (I) is a phenyl group which may have a substituent.

<3> The nonaqueous electrolytic solution according to the <1> or <2> above, wherein $R^1$ and $R^2$ in general formula (I) are each a hydrogen atom.

<4> The nonaqueous electrolytic solution according to any one of the <1> to <3> above, wherein the total content of the compound represented by general formula (I) and the compound represented by general formula (II) in the nonaqueous electrolytic solution is 0.001-10% by mass.

<5> The nonaqueous electrolytic solution according to any one of the <1> to <4> above, which further comprises at least one compound selected from the group consisting of cyclic carbonate compounds having a carbon-carbon unsaturated bond, cyclic carbonate compounds having a fluorine atom, monofluorophosphoric acid salts, and difluorophosphoric acid salts.

<6> A nonaqueous-electrolyte battery comprising: a negative electrode and a positive electrode which are capable of occluding and releasing lithium ions; and a nonaqueous electrolytic solution, wherein the nonaqueous electrolytic solution is the nonaqueous electrolytic solution according to any one of the <1> to <5> above.

<7> A compound represented by the following structural formula (III):

[Chem. 2]

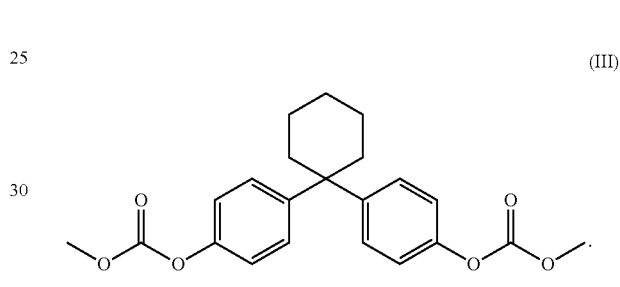

Effects of the Invention

According to the invention, it is possible to provide a nonaqueous-electrolyte battery which contains a nonaqueous electrolytic solution and which has enhanced safety during overcharge and, despite this, has high capacity and, in particular, excellent high-temperature storability. The invention can attain increases in performance in both potable appliance applications and large-size applications of nonaqueous-electrolyte batteries.

MODES FOR CARRYING OUT THE INVENTION

Embodiments of the invention are explained below. However, the invention should not be construed as being limited to the following embodiments, and can be modified at will so long as the modifications do not depart from the spirit of the invention.

Herein, "% by weight", "parts by weight", "weight ratio", and "unit weight" have the same meanings as "% by mass", "parts by mass", "mass ratio", and "unit mass", respectively. The mere expression "ppm" means "ppm by weight".

<Nonaqueous Electrolytic Solution>

The nonaqueous electrolytic solution of the invention is a nonaqueous electrolytic solution which includes an electrolyte and a nonaqueous solvent and which is characterized by containing a compound represented by general formula (I) and/or a compound represented by general formula (II).

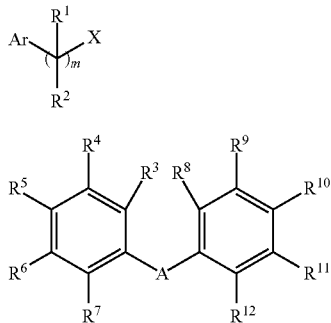

(In general formula (I), Ar represents an aryl group which may have a substituent, m represents an integer of 2 or larger, X represents an alkoxycarbonyloxy group, an organic sulfonate group, or a phosphoric acid ester group, and $R^1$ and $R^2$ each independently represent a hydrogen atom, a halogen atom, or an optionally substituted hydrocarbon group having 1-12 carbon atoms.

In general formula (II), A represents a divalent substituent which may contain a heteroatom, and $R^3$ to $R^{12}$ each independently represent a hydrogen atom, a halogen atom, an optionally substituted hydrocarbon group having 1-12 carbon atoms, an alkoxy group, an alkoxycarbonyloxy group, an organic sulfonate group, or a phosphoric acid ester group, at least one of the $R^3$ to $R^{12}$ representing an alkoxycarbonyloxy group, an organic sulfonate group, or a phosphoric acid ester group.)

(Compound Represented by General Formula (I))

In general formula (I), m represents an integer of 2 or larger. As will be demonstrated later in Examples, in case where m=1, i.e., where an ester group has been bonded through an alkyl chain not longer than a certain length, the effects of the invention are not produced. In the invention, the intramolecular distance between Ar and X in general formula (I) is important from the standpoint of controlling oxidation/reduction properties within batteries. With respect to a lower limit of m, it is preferable that m should be an integer of 3 or larger. With respect to an upper limit thereof, m is preferably an integer of 5 or smaller, more preferably an integer of 4 or smaller.

In general formula (I), $R^1$ and $R^2$ each independently represent a hydrogen atom, a halogen atom, or an optionally substituted hydrocarbon group having 1-12 carbon atoms, and are each preferably a hydrogen atom or a halogen atom, more preferably a hydrogen atom.

Examples of the halogen atom include chlorine, fluorine, bromine, and iodine atoms. Preferred are chlorine and fluorine atoms. More preferred is a fluorine atom.

Examples of the optionally substituted hydrocarbon group having 1-12 carbon atoms include alkyl groups having 1-12 carbon atoms, alkenyl groups having 2-12 carbon atoms, aryl groups having 6-12 carbon atoms, or aralkyl groups having 7-12 carbon atoms.

Examples of the alkyl groups having 1-12 carbon atoms include methyl, ethyl, n-propyl, isopropyl, n-butyl, isobutyl, sec-butyl, t-butyl, n-pentyl, t-amyl, n-hexyl, 1,1-dimethylbutyl, cyclobutyl, cyclopentyl, cyclohexyl, 1-methylcyclohexyl, and 1-ethylcyclohexyl. Preferred examples among these, from the standpoint of solubility in the electrolytic solution, include chain or cyclic alkyl groups having preferably 1-6 carbon atoms, more preferably 1-4 carbon atoms, even more preferably 1 or 2 carbon atoms.

Examples of the alkenyl groups having 2-12 carbon atoms include vinyl and propenyl. Preferred examples thereof include alkenyl groups having 2-8 carbon atoms. Especially preferred examples thereof include ones having 2-4 carbon atoms.

Examples of the aryl groups having 6-12 carbon atoms include phenyl, tolyl, xylyl, cyclohexylphenyl, and t-butylphenyl. Preferred of these are phenyl, cyclohexylphenyl, and t-butylphenyl, from the standpoint of oxidation/reduction stability within batteries.

Examples of the aralkyl groups having 7-12 carbon atoms include benzyl, phenethyl, phenylpropyl, phenylbutyl, and phenylpentyl. From the standpoint of improving overcharge characteristics, phenethyl, phenylpropyl, and phenylbutyl are preferred of those, and phenylpropyl is most preferred.

Those alkyl groups, alkenyl groups, aryl groups, and aralkyl groups may have been substituted with one or more fluorine atoms. Examples of the fluorine-substituted groups include fluoroalkyl groups such as trifluoromethyl, trifluoroethyl, and pentafluoroethyl, fluoroalkenyl groups such as 2-fluorovinyl and 3-fluoro-2-propenyl, fluoroaryl groups such as 2-fluorophenyl, 3-fluorophenyl, and 4-fluorophenyl, and fluoroaralkyl groups such as fluorophenylpropyl.

In general formula (I), X represents an alkoxycarbonyloxy group, an organic sulfonate group, or a phosphoric acid ester group. These groups are not particularly limited so long as the groups respectively have the structures of the following formulae (a) to (c). Any desired one of these groups can be used.

[Chem. 4]

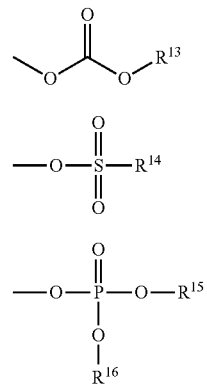

In formulae (a) to (c), $R^{13}$ to $R^{16}$ each independently represent an optionally substituted hydrocarbon group having 1-12 carbon atoms. Examples thereof include alkyl groups having 1-12 carbon atoms, alkenyl groups having 2-12 carbon atoms, aryl groups having 6-12 carbon atoms, or aralkyl groups having 7-12 carbon atoms.

Examples of the alkyl groups having 1-12 carbon atoms include methyl, ethyl, n-propyl, isopropyl, n-butyl, isobutyl, sec-butyl, t-butyl, n-pentyl, t-amyl, n-hexyl, 1,1-dimethylbutyl, cyclobutyl, cyclopentyl, cyclohexyl, 1-methylcyclohexyl, and 1-ethylcyclohexyl. Preferred examples among these, from the standpoint of solubility in the electrolytic solution, include chain or cyclic alkyl groups having preferably 1-6 carbon atoms, more preferably 1-4 carbon atoms, even more preferably 1 or 2 carbon atoms.

Examples of the alkenyl groups having 2-12 carbon atoms include vinyl and propenyl. Preferred examples thereof include alkenyl groups having 2-8 carbon atoms. Especially preferred examples thereof include ones having 2-4 carbon atoms.

Examples of the aryl groups having 6-12 carbon atoms include phenyl, tolyl, xylyl, cyclohexylphenyl, and t-butylphenyl. Preferred of these are phenyl, cyclohexylphenyl, and t-butylphenyl, from the standpoint of oxidation/reduction stability within batteries.

Examples of the aralkyl groups having 7-12 carbon atoms include benzyl, phenethyl, phenylpropyl, phenylbutyl, and phenylpentyl. From the standpoint of improving overcharge characteristics, phenethyl, phenylpropyl, and phenylbutyl are preferred of those, and phenylpropyl is most preferred.

Those alkyl groups, alkenyl groups, aryl groups, and aralkyl groups may have been substituted with one or more fluorine atoms. Examples of the fluorine-substituted groups include fluoroalkyl groups such as trifluoromethyl, trifluoroethyl, and pentafluoroethyl, fluoroalkenyl groups such as 2-fluorovinyl and 3-fluoro-2-propenyl, fluoroaryl groups such as 2-fluorophenyl, 3-fluorophenyl, and 4-fluorophenyl, and fluoroaralkyl groups such as fluorophenylpropyl.

Ar in general formula (I) represents an aryl group which may have a substituent. Examples of the aryl group include phenyl, naphthyl, anthryl, phenanthryl, biphenyl, and terphenyl. Preferred of these aryl groups is phenyl, from the standpoint that the compound causes no side reaction at ordinary working voltages of batteries.

Examples of substituents which may be possessed by Ar include halogen atoms and hydrocarbon groups which may have a heteroatom or halogen atom. Examples of the hydrocarbon groups include alkyl groups having 1-12 carbon atoms, alkenyl groups having 2-12 carbon atoms, aryl groups having 6-12 carbon atoms, or aralkyl groups having 7-12 carbon atoms.

Ar in general formula (I) may have two or more substituents, which may form a heterocycle in cooperation with the Ar within general formula (I).

Examples of the alkyl groups having 1-12 carbon atoms include methyl, ethyl, n-propyl, isopropyl, n-butyl, isobutyl, sec-butyl, t-butyl, n-pentyl, t-amyl, n-hexyl, 1,1-dimethylbutyl, cyclobutyl, cyclopentyl, cyclohexyl, 1-methylcyclohexyl, 1-ethylcyclohexyl, and a substituent bonded to the Ar within general formula (I) to form a tetrahydronaphthyl group.

Examples of the alkenyl groups having 2-12 carbon atoms include vinyl and propenyl. Preferred examples thereof include alkenyl groups having 2-8 carbon atoms. Especially preferred examples thereof include ones having 2-4 carbon atoms.

Examples of the aryl groups having 6-12 carbon atoms include phenyl, tolyl, xylyl, cyclohexylphenyl, t-butylphenyl, and a substituent which forms a naphthalene group in cooperation with a benzene ring within the compound (I). Preferred of these are phenyl, cyclohexylphenyl, and t-butylphenyl, from the standpoint of oxidation/reduction stability within batteries.

Examples of the aralkyl groups having 7-12 carbon atoms include benzyl and phenethyl. Of these, benzyl is preferred from the standpoint of oxidation/reduction stability within batteries.

Those alkyl groups, alkenyl groups, aryl groups, and aralkyl groups may have been substituted with one or more fluorine atoms. Examples of the fluorine-substituted groups include fluoroalkyl groups such as trifluoromethyl, trifluoroethyl, and pentafluoroethyl, fluoroalkenyl groups such as 2-fluorovinyl and 3-fluoro-2-propenyl, fluoroaryl groups such as 2-fluorophenyl, 3-fluorophenyl, and 4-fluorophenyl, and fluoroaralkyl groups such as 2-fluorobenzyl, 3-fluorobenzyl, and 4-fluorobenzyl.

From the standpoints of improving safety during overcharge and improving battery characteristics, it is desirable that Ar should be an aryl group having no substituent or having as a substituent an alkyl group having 3 or more carbon atoms. Ar preferably is an aryl group having no substituent or having as a substituent an alkyl group having 4 or more carbon atoms, and more preferably is an aryl group having no substituent or having as a substituent an alkyl group having 5 or more carbon atoms.

It is preferable that the alkyl group having 3 or more carbon atoms should be a secondary alkyl group or a tertiary alkyl group, from the standpoint of oxidation stability within batteries. More preferred of such alkyl groups are sec-butyl, t-butyl, t-amyl, 1,1-dimethylbutyl, cyclopentyl, cyclohexyl, 1-methylcyclohexyl, and 1-ethylcyclohexyl. Even more preferred are t-butyl, t-amyl, 1,1-dimethylbutyl, cyclopentyl, cyclohexyl, 1-methylcyclohexyl, and 1-ethylcyclohexyl. Especially preferred are t-amyl, 1,1-dimethylbutyl, cyclopentyl, cyclohexyl, 1-methylcyclohexyl, and 1-ethylcyclohexyl, which are secondary or tertiary alkyl groups having 5 or more carbon atoms.

Specific examples of the compound represented by general formula (I) include the following compounds.

<Compounds in which X is Alkoxycarbonyloxy Group>

Compounds represented by formula (a) in which $R^{13}$ is an alkyl group having 1-12 carbon atoms and m=3, such as methyl 3-phenylpropyl carbonate, methyl 3-(2-n-pentylphenyl)propyl carbonate, methyl 3-(3-n-pentylphenyl)propyl carbonate, methyl 3-(4-n-pentylphenyl)propyl carbonate, methyl 3-(2,4-di-n-pentylphenyl)propyl carbonate, methyl 3-(3,5-di-n-pentylphenyl)propyl carbonate, methyl 3-(2-t-amylphenyl)propyl carbonate, methyl 3-(3-t-amylphenyl)propyl carbonate, methyl 3-(4-t-amylphenyl)propyl carbonate, methyl 3-(2,4-di-t-amylphenyl)propyl carbonate, methyl 3-(3,5-di-t-amylphenyl)propyl carbonate, methyl 3-(2-cyclopentylphenyl)propyl carbonate, methyl 3-(3-cyclopentylphenyl)propyl carbonate, methyl 3-(4-cyclopentylphenyl)propyl carbonate, methyl 3-(2-cyclohexylphenyl)propyl carbonate, methyl 3-(3-cyclohexylphenyl)propyl carbonate, methyl 3-(4-cyclohexylphenyl)propyl carbonate, ethyl 3-phenylpropyl carbonate, ethyl 3-(2-n-pentylphenyl)propyl carbonate, ethyl 3-(3-n-pentylphenyl)propyl carbonate, ethyl 3-(4-n-pentylphenyl)propyl carbonate, ethyl 3-(2,4-di-n-pentylphenyl)propyl carbonate, ethyl 3-(3,5-di-n-pentylphenyl)propyl carbonate, ethyl 3-(2-t-amylphenyl)propyl carbonate, ethyl 3-(3-t-amylphenyl)propyl carbonate, ethyl 3-(4-t-amylphenyl)propyl carbonate, ethyl 3-(2,4-di-t-amylphenyl)propyl carbonate, ethyl 3-(3,5-di-t-amylphenyl)propyl carbonate, ethyl 3-(2-cyclopentylphenyl)propyl carbonate, ethyl 3-(3-cyclopentylphenyl)propyl carbonate, ethyl 3-(4-cyclopentylphenyl)propyl carbonate, ethyl 3-(2-cyclohexylphenyl)propyl carbonate, ethyl 3-(3-cyclohexylphenyl)propyl carbonate, and ethyl 3-(4-cyclohexylphenyl)propyl carbonate;

compounds represented by formula (a) in which $R^{13}$ is an alkenyl group having 2-12 carbon atoms and m=3, such as vinyl 3-phenylpropyl carbonate, vinyl 3-(2-n-pentylphenyl)propyl carbonate, vinyl 3-(3-n-pentylphenyl)propyl carbonate, vinyl 3-(4-n-pentylphenyl)propyl carbonate, vinyl 3-(2,4-di-n-pentylphenyl)propyl carbonate, vinyl 3-(3,5-di-n-pentylphenyl)propyl carbonate, vinyl 3-(2-t-amylphenyl)propyl carbonate, vinyl 3-(3-t-amylphenyl)propyl carbonate, vinyl 3-(4-t-amylphenyl)propyl carbonate, vinyl 3-(2,4-di-t-amylphenyl)propyl carbonate, vinyl 3-(3,5-di-t-amylphenyl)propyl carbonate, vinyl 3-(2-cyclopentylphenyl)propyl carbonate, vinyl 3-(3-cyclopentylphenyl)propyl carbonate, vinyl 3-(4-cyclopentylphenyl)propyl carbonate, vinyl 3-(2-cyclohexylphenyl)propyl carbonate, vinyl 3-(3-cyclohexylphenyl)propyl carbonate, vinyl 3-(4-cyclohexylphenyl)propyl carbonate, allyl 3-phenylpropyl carbonate, allyl 3-(2-n-pentylphenyl)propyl carbonate, allyl 3-(3-n-pentylphenyl)propyl carbonate, allyl 3-(4-n-pentylphenyl)propyl carbonate, allyl 3-(2,4-di-n-pentylphenyl)propyl carbonate, allyl 3-(3,5-di-n-pentylphenyl)propyl carbonate, allyl 3-(2-t-amylphenyl)propyl carbonate, allyl 3-(3-t-amylphenyl)propyl carbonate, allyl 3-(4-t-amylphenyl)propyl carbonate, allyl 3-(2,4-di-t-amylphenyl)propyl carbonate, allyl 3-(3,5-di-t-amylphenyl)propyl carbonate, allyl 3-(2-cyclopentylphenyl)propyl carbonate, allyl 3-(3-cyclopentylphenyl)propyl carbonate, allyl 3-(4-cyclopentylphenyl)propyl carbonate, allyl 3-(2-cyclohexylphenyl)propyl carbonate, allyl 3-(3-cyclohexylphenyl)propyl carbonate, and allyl 3-(4-cyclohexylphenyl)propyl carbonate;

compounds represented by formula (a) in which $R^{13}$ is an aryl group having 6-12 carbon atoms and m=3, such as phenyl 3-phenylpropyl carbonate, phenyl 3-(2-n-pentylphenyl)propyl carbonate, phenyl 3-(3-n-pentylphenyl)propyl carbonate, phenyl 3-(4-n-pentylphenyl)propyl carbonate, phenyl 3-(2,4-di-n-pentylphenyl)propyl carbonate, phenyl 3-(3,5-di-n-pentylphenyl)propyl carbonate, phenyl 3-(2-t-amylphenyl)propyl carbonate, phenyl 3-(3-t-amylphenyl)propyl carbonate, phenyl 3-(4-t-amylphenyl)propyl carbonate, phenyl 3-(2,4-di-t-amylphenyl)propyl carbonate, phenyl 3-(3,5-di-t-amylphenyl)propyl carbonate, phenyl 3-(2-cyclopentylphenyl)propyl carbonate, phenyl 3-(3-cyclopentylphenyl)propyl carbonate, phenyl 3-(4-cyclopentylphenyl)propyl carbonate, phenyl 3-(2-cyclohexylphenyl)propyl carbonate, phenyl 3-(3-cyclohexylphenyl)propyl carbonate, and phenyl 3-(4-cyclohexylphenyl)propyl carbonate;

compounds represented by formula (a) in which $R^{13}$ is an aralkyl group having 7-12 carbon atoms and m=3, such as benzyl 3-phenylpropyl carbonate, benzyl 3-(2-n-pentylphenyl)propyl carbonate, benzyl 3-(3-n-pentylphenyl)propyl carbonate, benzyl 3-(4-n-pentylphenyl)propyl carbonate, benzyl 3-(2,4-di-n-pentylphenyl)propyl carbonate, benzyl 3-(3,5-di-n-pentylphenyl)propyl carbonate, benzyl 3-(2-t-amylphenyl)propyl carbonate, benzyl 3-(3-t-amylphenyl)propyl carbonate, benzyl 3-(4-t-amylphenyl)propyl carbonate, benzyl 3-(2,4-di-t-amylphenyl)propyl carbonate, benzyl 3-(3,5-di-t-amylphenyl)propyl carbonate, benzyl 3-(2-cyclopentylphenyl)propyl carbonate, benzyl 3-(3-cyclopentylphenyl)propyl carbonate, benzyl 3-(4-cyclopentylphenyl)propyl carbonate, benzyl 3-(2-cyclohexylphenyl)propyl carbonate, benzyl 3-(3-cyclohexylphenyl)propyl carbonate, benzyl 3-(4-cyclohexylphenyl)propyl carbonate, di-3-phenylpropyl carbonate, 3-phenylpropyl 3-(2-n-pentylphenyl)propyl carbonate, 3-phenylpropyl 3-(3-n-pentylphenyl)propyl carbonate, 3-phenylpropyl 3-(4-n-pentylphenyl)propyl carbonate, 3-phenylpropyl 3-(2,4-di-n-pentylphenyl)propyl carbonate, 3-phenylpropyl 3-(3,5-di-n-pentylphenyl)propyl carbonate, 3-phenylpropyl 3-(2-t-amylphenyl)propyl carbonate, 3-phenylpropyl 3-(3-t-amylphenyl)propyl carbonate, 3-phenylpropyl 3-(4-t-amylphenyl)propyl carbonate, 3-phenylpropyl 3-(2,4-di-t-amylphenyl)propyl carbonate, 3-phenylpropyl 3-(3,5-di-t-amylphenyl)propyl carbonate, 3-phenylpropyl 3-(2-cyclopentylphenyl)propyl carbonate, 3-phenylpropyl 3-(3-cyclopentylphenyl)propyl carbonate, 3-phenylpropyl 3-(4-cyclopentylphenyl)propyl carbonate, 3-phenylpropyl 3-(2-cyclohexylphenyl)propyl carbonate, 3-phenylpropyl 3-(3-cyclohexylphenyl)propyl carbonate, and 3-phenylpropyl 3-(4-cyclohexylphenyl)propyl carbonate; and compounds represented by formula (a) in which $R^{13}$ is a fluorine-substituted alkyl group having 1-12 carbon atoms and m=3, such as trifluoromethyl 3-phenylpropyl carbonate, trifluoromethyl 3-(2-n-pentylphenyl)propyl carbonate, trifluoromethyl 3-(3-n-pentylphenyl)propyl carbonate, trifluoromethyl 3-(4-n-pentylphenyl)propyl carbonate, trifluoromethyl 3-(2,4-di-n-pentylphenyl)propyl carbonate, trifluoromethyl 3-(3,5-di-n-pentylphenyl)propyl carbonate, trifluoromethyl 3-(2-t-amylphenyl)propyl carbonate, trifluoromethyl 3-(3-t-amylphenyl)propyl carbonate, trifluoromethyl 3-(4-t-amylphenyl)propyl carbonate, trifluoromethyl 3-(2,4-di-t-amylphenyl)propyl carbonate, trifluoromethyl 3-(3,5-di-t-amylphenyl)propyl carbonate, trifluoromethyl 3-(2-cyclopentylphenyl)propyl carbonate, trifluoromethyl 3-(3-cyclopentylphenyl)propyl carbonate, trifluoromethyl 3-(4-cyclopentylphenyl)propyl carbonate, trifluoromethyl 3-(2-cyclohexylphenyl)propyl carbonate, trifluoromethyl 3-(3-cyclohexylphenyl)propyl carbonate, and trifluoromethyl 3-(4-cyclohexylphenyl)propyl carbonate.

<Compounds in which X is Organic Sulfonate Group>

Compounds represented by formula (b) in which $R^{14}$ is an alkyl group having 1-12 carbon atoms and m=3, such as 3-phenylpropyl methanesulfonate, 3-(2-n-pentylphenyl)propyl methanesulfonate, 3-(3-n-pentylphenyl)propyl methanesulfonate, 3-(4-n-pentylphenyl)propyl methanesulfonate, 3-(2,4-di-n-pentylphenyl)propyl methanesulfonate, 3-(3,5-di-n-pentylphenyl)propyl methanesulfonate, 3-(2-t-amylphenyl)propyl methanesulfonate, 3-(3-t-amylphenyl)propyl methanesulfonate, 3-(4-t-amylphenyl)propyl methanesulfonate, 3-(2,4-di-t-amylphenyl)propyl methanesulfonate, 3-(3,5-di-t-amylphenyl)propyl methanesulfonate, 3-(2-cyclopentylphenyl)propyl methanesulfonate, 3-(3-cyclopentylphenyl)propyl methanesulfonate, 3-(4-cyclopentylphenyl)propyl methanesulfonate, 3-(2-cyclohexylphenyl)propyl methane sulfonate, 3-(3-cyclohexylphenyl)propyl methanesulfonate, 3-(4-cyclohexylphenyl)propyl methanesulfonate, 3-phenylpropyl ethanesulfonate, 3-(2-n-pentylphenyl)propyl ethanesulfonate, 3-(3-n-pentylphenyl)propyl ethanesulfonate, 3-(4-n-pentylphenyl)propyl ethanesulfonate, 3-(2,4-di-n-pentylphenyl)propyl ethanesulfonate, 3-(3,5-di-n-pentylphenyl)propyl ethanesulfonate, 3-(2-t-amylphenyl)propyl ethanesulfonate, 3-(3-t-amylphenyl)propyl ethanesulfonate, 3-(4-t-amylphenyl)propyl ethanesulfonate, 3-(2,4-di-t-amylphenyl)propyl ethanesulfonate, 3-(3,5-di-t-amylphenyl)propyl ethanesulfonate, 3-(2-cyclopentylphenyl)propyl ethanesulfonate, 3-(3-cyclopentylphenyl)propyl ethanesulfonate, 3-(4-cyclopentylphenyl)propyl ethanesulfonate, 3-(2-cyclohexylphenyl)propyl ethanesulfonate, 3-(3-cyclohexylphenyl)propyl ethanesulfonate, and 3-(4-cyclohexylphenyl)propyl ethanesulfonate;

compounds represented by formula (b) in which $R^{14}$ is an alkenyl group having 2-12 carbon atoms and m=3, such as 3-phenylpropyl vinylsulfonate, 3-(2-n-pentylphenyl)propyl vinylsulfonate, 3-(3-n-pentylphenyl)propyl vinylsulfonate, 3-(4-n-pentylphenyl)propyl vinylsulfonate, 3-(2,4-di-n-pentylphenyl)propyl vinylsulfonate, 3-(3,5-di-n-pentylphenyl)propyl vinylsulfonate, 3-(2-t-amylphenyl)propyl vinylsulfonate, 3-(3-t-amylphenyl)propyl vinylsulfonate, 3-(4-t-amylphenyl)propyl vinylsulfonate, 3-(2,4-di-t-amylphenyl)propyl vinylsulfonate, 3-(3,5-di-t-amylphenyl)propyl vinylsulfonate, 3-(2-cyclopentylphenyl)propyl vinylsulfonate, 3-(3-cyclopentylphenyl)propyl vinylsulfonate, 3-(4-cyclopentylphenyl)propyl vinylsulfonate, 3-(2-cyclohexylphenyl)propyl vinylsulfonate, 3-(3-cyclohexylphenyl)

propyl vinylsulfonate, 3-(4-cyclohexylphenyl)propyl vinylsulfonate, 3-phenylpropyl allylsulfonate, 3-(2-n-pentylphenyl)propyl allylsulfonate, 3-(3-n-pentylphenyl)propyl allylsulfonate, 3-(4-n-pentylphenyl)propyl allylsulfonate, 3-(2,4-di-n-pentylphenyl)propyl allylsulfonate, 3-(3,5-di-n-pentylphenyl)propyl allylsulfonate, 3-(2-t-amylphenyl)propyl allylsulfonate, 3-(3-t-amylphenyl)propyl allylsulfonate, 3-(4-t-amylphenyl)propyl allylsulfonate, 3-(2,4-di-t-amylphenyl)propyl allylsulfonate, di-t-amylphenyl)propyl allylsulfonate, 3-(2-cyclopentylphenyl)propyl allylsulfonate, 3-(3-cyclopentylphenyl)propyl allylsulfonate, 3-(4-cyclopentylphenyl)propyl allylsulfonate, 3-(2-cyclohexylphenyl)propyl allylsulfonate, 3-(3-cyclohexylphenyl)propyl allylsulfonate, and 3-(4-cyclohexylphenyl)propyl allylsulfonate;

compounds represented by formula (b) in which $R^{14}$ is an aryl group having 6-12 carbon atoms and m=3, such as 3-phenylpropyl benzenesulfonate, 3-(2-n-pentylphenyl)propyl benzenesulfonate, 3-(3-n-pentylphenyl)propyl benzenesulfonate, 3-(4-n-pentylphenyl)propyl benzenesulfonate, 3-(2,4-di-n-pentylphenyl)propyl benzenesulfonate, 3-(3,5-di-n-pentylphenyl)propyl benzenesulfonate, 3-(2-t-amylphenyl)propyl benzenesulfonate, 3-(3-t-amylphenyl)propyl benzenesulfonate, 3-(4-t-amylphenyl)propyl benzenesulfonate, 3-(2,4-di-t-amylphenyl)propyl benzenesulfonate, 3-(3,5-di-t-amylphenyl)propyl benzenesulfonate, 3-(2-cyclopentylphenyl)propyl benzenesulfonate, 3-(3-cyclopentylphenyl)propyl benzenesulfonate, 3-(4-cyclopentylphenyl)propyl benzenesulfonate, 3-(2-cyclohexylphenyl)propyl benzenesulfonate, 3-(3-cyclohexylphenyl)propyl benzenesulfonate, and 3-(4-cyclohexylphenyl)propyl benzenesulfonate;

compounds represented by formula (b) in which $R^{14}$ is an aralkyl group having 7-12 carbon atoms and m=3, such as 3-phenylpropyl benzylsulfonate, 3-(2-n-pentylphenyl)propyl benzylsulfonate, 3-(3-n-pentylphenyl)propyl benzylsulfonate, 3-(4-n-pentylphenyl)propyl benzylsulfonate, 3-(2,4-di-n-pentylphenyl)propyl benzylsulfonate, 3-(3,5-di-n-pentylphenyl)propyl benzylsulfonate, 3-(2-t-amylphenyl)propyl benzylsulfonate, 3-(3-t-amylphenyl)propyl benzylsulfonate, 3-(4-t-amylphenyl)propyl benzylsulfonate, 3-(2,4-di-t-amylphenyl)propyl benzylsulfonate, 3-(3,5-di-t-amylphenyl)propyl benzylsulfonate, 3-(2-cyclopentylphenyl)propyl benzylsulfonate, 3-(3-cyclopentylphenyl)propyl benzylsulfonate, 3-(4-cyclopentylphenyl)propyl benzylsulfonate, 3-(2-cyclohexylphenyl)propyl benzylsulfonate, 3-(3-cyclohexylphenyl)propyl benzylsulfonate, 3-(4-cyclohexylphenyl)propyl benzylsulfonate, 3-phenylpropyl 3-phenylpropanesulfonate, 3-(2-n-pentylphenyl) 3-phenylpropanesulfonate, 3-(3-n-pentylphenyl) 3-phenylpropanesulfonate, 3-(4-n-pentylphenyl) 3-phenylpropanesulfonate, 3-(2,4-di-n-pentylphenyl) 3-phenylpropanesulfonate, 3-(3,5-di-n-pentylphenyl) 3-phenylpropanesulfonate, 3-(2-t-amylphenyl) 3-phenylpropanesulfonate, 3-(3-t-amylphenyl) 3-phenylpropanesulfonate, 3-(4-t-amylphenyl) 3-phenylpropanesulfonate, 3-(2,4-di-t-amylphenyl) 3-phenylpropanesulfonate, 3-(3,5-di-t-amylphenyl) 3-phenylpropanesulfonate, 3-(2-cyclopentylphenyl) 3-phenylpropanesulfonate, 3-(3-cyclopentylphenyl) 3-phenylpropanesulfonate, 3-(4-cyclopentylphenyl) 3-phenylpropanesulfonate, 3-(2-cyclohexylphenyl) 3-phenylpropanesulfonate, 3-(3-cyclohexylphenyl) 3-phenylpropanesulfonate, and 3-(4-cyclohexylphenyl)propyl 3-phenylpropanesulfonate; and compounds represented by formula (b) in which $R^{14}$ is a fluorine-substituted alkyl group having 1-12 carbon atoms and m=3, such as 3-phenylpropyl trifluoromethanesulfonate, 3-(2-n-pentylphenyl)propyl trifluoromethanesulfonate, 3-(3-n-pentylphenyl)propyl trifluoromethanesulfonate, 3-(4-n-pentylphenyl)propyl trifluoromethanesulfonate, 3-(2,4-di-n-pentylphenyl)propyl trifluoromethanesulfonate, 3-(3,5-di-n-pentylphenyl)propyl trifluoromethanesulfonate, 3-(2-t-amylphenyl)propyl trifluoromethanesulfonate, 3-(3-t-amylphenyl)propyl trifluoromethanesulfonate, 3-(4-t-amylphenyl)propyl trifluoromethanesulfonate, 3-(2,4-di-t-amylphenyl)propyl trifluoromethanesulfonate, 3-(3,5-di-t-amylphenyl)propyl trifluoromethanesulfonate, 3-(2-cyclopentylphenyl)propyl trifluoromethanesulfonate, 3-(3-cyclopentylphenyl)propyl trifluoromethanesulfonate, 3-(4-cyclopentylphenyl)propyl trifluoromethanesulfonate, 3-(2-cyclohexylphenyl)propyl trifluoromethanesulfonate, 3-(3-cyclohexylphenyl)propyl trifluoromethanesulfonate, and 3-(4-cyclohexylphenyl)propyl trifluoromethanesulfonate.

<Compounds in which X is Phosphoric Acid Ester Group>

Compounds represented by formula (c) in which $R^{15}$ and $R^{16}$ are each independently an alkyl group having 1-12 carbon atoms and m=3, such as dimethyl 3-phenylpropyl phosphate, dimethyl 3-(2-n-pentylphenyl)propyl phosphate, dimethyl 3-(3-n-pentylphenyl)propyl phosphate, dimethyl 3-(4-n-pentylphenyl)propyl phosphate, dimethyl 3-(2,4-di-n-pentylphenyl)propyl phosphate, dimethyl 3-(3,5-di-n-pentylphenyl)propyl phosphate, dimethyl 3-(2-t-amylphenyl)propyl phosphate, dimethyl 3-(3-t-amylphenyl)propyl phosphate, dimethyl 3-(4-t-amylphenyl)propyl phosphate, dimethyl 3-(2,4-di-t-amylphenyl)propyl phosphate, dimethyl 3-(3,5-di-t-amylphenyl)propyl phosphate, dimethyl 3-(2-cyclopentylphenyl)propyl phosphate, dimethyl 3-(3-cyclopentylphenyl)propyl phosphate, dimethyl 3-(4-cyclopentylphenyl)propyl phosphate, dimethyl 3-(2-cyclohexylphenyl)propyl phosphate, dimethyl 3-(3-cyclohexylphenyl)propyl phosphate, dimethyl 3-(4-cyclohexylphenyl)propyl phosphate, diethyl 3-phenylpropyl phosphate, diethyl 3-(2-n-pentylphenyl)propyl phosphate, diethyl 3-(3-n-pentylphenyl)propyl phosphate, diethyl 3-(4-n-pentylphenyl)propyl phosphate, diethyl 3-(2,4-di-n-pentylphenyl)propyl phosphate, diethyl 3-(3,5-di-n-pentylphenyl)propyl phosphate, diethyl 3-(2-t-amylphenyl)propyl phosphate, diethyl 3-(3-t-amylphenyl)propyl phosphate, diethyl 3-(4-t-amylphenyl)propyl phosphate, diethyl 3-(2,4-di-t-amylphenyl)propyl phosphate, diethyl 3-(3,5-di-t-amylphenyl)propyl phosphate, diethyl 3-(2-cyclopentylphenyl)propyl phosphate, diethyl 3-(3-cyclopentylphenyl)propyl phosphate, diethyl 3-(4-cyclopentylphenyl)propyl phosphate, diethyl 3-(2-cyclohexylphenyl)propyl phosphate, diethyl 3-(3-cyclohexylphenyl)propyl phosphate, diethyl 3-(4-cyclohexylphenyl)propyl phosphate, ethyl methyl 3-phenylpropyl phosphate, ethyl methyl 3-(2-n-pentylphenyl)propyl phosphate, ethyl methyl 3-(3-n-pentylphenyl)propyl phosphate, ethyl methyl 3-(4-n-pentylphenyl)propyl phosphate, ethyl methyl 3-(2,4-di-n-pentylphenyl)propyl phosphate, ethyl methyl 3-(3,5-di-n-pentylphenyl)propyl phosphate, ethyl methyl 3-(2-t-amylphenyl)propyl phosphate, ethyl methyl 3-(3-t-amylphenyl)propyl phosphate, ethyl methyl 3-(4-t-amylphenyl)propyl phosphate, ethyl methyl 3-(2,4-di-t-amylphenyl)propyl phosphate, ethyl methyl 3-(3,5-di-t-amylphenyl)propyl phosphate, ethyl methyl 3-(2-cyclopentylphenyl)propyl phosphate, ethyl methyl 3-(3-cyclopentylphenyl)propyl phosphate, ethyl methyl 3-(4-cyclopentylphenyl)propyl phosphate, ethyl methyl 3-(2-cyclohexylphenyl)propyl phosphate, ethyl methyl 3-(3-cyclohexylphenyl)propyl phosphate, and ethyl methyl 3-(4-cyclohexylphenyl)propyl phosphate;

compounds represented by formula (c) in which $R^{15}$ and $R^{16}$ are each independently an alkenyl group having 2-12 carbon atoms and m=3, such as divinyl 3-phenylpropyl phosphate, divinyl 3-(2-n-pentylphenyl)propyl phosphate, divinyl 3-(3-n-pentylphenyl)propyl phosphate, divinyl 3-(4-n-pentylphenyl)propyl phosphate, divinyl 3-(2,4-di-n-pentylphenyl)propyl phosphate, divinyl 3-(3,5-di-n-pentylphenyl)propyl phosphate, divinyl 3-(2-t-amylphenyl)propyl phosphate, divinyl 3-(3-t-amylphenyl)propyl phosphate, divinyl 3-(4-t-amylphenyl)propyl phosphate, divinyl 3-(2,4-di-t-amylphenyl)propyl phosphate, divinyl 3-(3,5-di-t-amylphenyl)propyl phosphate, divinyl 3-(2-cyclopentylphenyl)propyl phosphate, divinyl 3-(3-cyclopentylphenyl)propyl phosphate, divinyl 3-(4-cyclopentylphenyl)propyl phosphate, divinyl 3-(2-cyclohexylphenyl)propyl phosphate, divinyl 3-(3-cyclohexylphenyl)propyl phosphate, divinyl 3-(4-cyclohexylphenyl)propyl phosphate, diallyl 3-phenylpropyl phosphate, diallyl 3-(2-n-pentylphenyl)propyl phosphate, diallyl 3-(3-n-pentylphenyl)propyl phosphate, diallyl 3-(4-n-pentylphenyl)propyl phosphate, diallyl 3-(2,4-di-n-pentylphenyl)propyl phosphate, diallyl 3-(3,5-di-n-pentylphenyl)propyl phosphate, diallyl 3-(2-t-amylphenyl)propyl phosphate, diallyl 3-(3-t-amylphenyl)propyl phosphate, diallyl 3-(4-t-amylphenyl)propyl phosphate, diallyl 3-(2,4-di-t-amylphenyl)propyl phosphate, diallyl 3-(3,5-di-t-amylphenyl)propyl phosphate, diallyl 3-(2-cyclopentylphenyl)propyl phosphate, diallyl 3-(3-cyclopentylphenyl)propyl phosphate, diallyl 3-(4-cyclopentylphenyl)propyl phosphate, diallyl 3-(2-cyclohexylphenyl)propyl phosphate, diallyl 3-(3-cyclohexylphenyl)propyl phosphate, and diallyl 3-(4-cyclohexylphenyl)propyl phosphate;

compounds represented by formula (c) in which $R^{15}$ and $R^{16}$ are each independently an aryl group having 6-12 carbon atoms, such as diphenyl 3-phenylpropyl phosphate, diphenyl 3-(2-n-pentylphenyl)propyl phosphate, diphenyl 3-(3-n-pentylphenyl)propyl phosphate, diphenyl 3-(4-n-pentylphenyl)propyl phosphate, diphenyl 3-(2,4-di-n-pentylphenyl)propyl phosphate, diphenyl 3-(3,5-di-n-pentylphenyl)propyl phosphate, diphenyl 3-(2-t-amylphenyl)propyl phosphate, diphenyl 3-(3-t-amylphenyl)propyl phosphate, diphenyl 3-(4-t-amylphenyl)propyl phosphate, diphenyl 3-(2,4-di-t-amylphenyl)propyl phosphate, diphenyl 3-(3,5-di-t-amylphenyl)propyl phosphate, diphenyl 3-(2-cyclopentylphenyl)propyl phosphate, diphenyl 3-(3-cyclopentylphenyl)propyl phosphate, diphenyl 3-(4-cyclopentylphenyl)propyl phosphate, diphenyl 3-(2-cyclohexylphenyl)propyl phosphate, diphenyl 3-(3-cyclohexylphenyl)propyl phosphate, and diphenyl 3-(4-cyclohexylphenyl)propyl phosphate;

compounds represented by formula (c) in which $R^{15}$ and $R^{16}$ are each independently an aralkyl group having 7-12 carbon atoms and m=3, such as dibenzyl 3-phenylpropyl phosphate, dibenzyl 3-(2-n-pentylphenyl)propyl phosphate, dibenzyl 3-(3-n-pentylphenyl)propyl phosphate, dibenzyl 3-(4-n-pentylphenyl)propyl phosphate, dibenzyl 3-(2,4-di-n-pentylphenyl)propyl phosphate, dibenzyl 3-(3,5-di-n-pentylphenyl)propyl phosphate, dibenzyl 3-(2-t-amylphenyl)propyl phosphate, dibenzyl 3-(3-t-amylphenyl)propyl phosphate, dibenzyl 3-(4-t-amylphenyl)propyl phosphate, dibenzyl 3-(2,4-di-t-amylphenyl)propyl phosphate, dibenzyl 3-(3,5-di-t-amylphenyl)propyl phosphate, dibenzyl 3-(2-cyclopentylphenyl)propyl phosphate, dibenzyl 3-(3-cyclopentylphenyl)propyl phosphate, dibenzyl 3-(4-cyclopentylphenyl)propyl phosphate, dibenzyl 3-(2-cyclohexylphenyl)propyl phosphate, dibenzyl 3-(3-cyclohexylphenyl)propyl phosphate, dibenzyl 3-(4-cyclohexylphenyl)propyl phosphate, tri-3-phenylpropyl phosphate, di-3-phenylpropyl 3-(2-n-pentylphenyl)propyl phosphate, di-3-phenylpropyl 3-(3-n-pentylphenyl)propyl phosphate, di-3-phenylpropyl 3-(4-n-pentylphenyl)propyl phosphate, di-3-phenylpropyl 3-(2,4-di-n-pentylphenyl)propyl phosphate, di-3-phenylpropyl 3-(3,5-di-n-pentylphenyl)propyl phosphate, di-3-phenylpropyl 3-(2-t-amylphenyl)propyl phosphate, di-3-phenylpropyl 3-(3-t-amylphenyl)propyl phosphate, di-3-phenylpropyl 3-(4-t-amylphenyl)propyl phosphate, di-3-phenylpropyl 3-(2,4-di-t-amylphenyl)propyl phosphate, di-3-phenylpropyl 3-(3,5-di-t-amylphenyl)propyl phosphate, di-3-phenylpropyl 3-(2-cyclopentylphenyl)propyl phosphate, di-3-phenylpropyl 3-(3-cyclopentylphenyl)propyl phosphate, di-3-phenylpropyl 3-(4-cyclopentylphenyl)propyl phosphate, di-3-phenylpropyl 3-(2-cyclohexylphenyl)propyl phosphate, di-3-phenylpropyl 3-(3-cyclohexylphenyl)propyl phosphate, and di-3-phenylpropyl 3-(4-cyclohexylphenyl)propyl phosphate; and compounds represented by formula (c) in which $R^{15}$ and $R^{16}$ are each independently a fluorine-substituted alkyl group having 1-12 carbon atoms and m=3, such as trifluoromethyl 3-phenylpropyl phosphate, trifluoromethyl 3-(2-n-pentylphenyl)propyl phosphate, trifluoromethyl 3-(3-n-pentylphenyl)propyl phosphate, trifluoromethyl 3-(4-n-pentylphenyl)propyl phosphate, trifluoromethyl 3-(2,4-di-n-pentylphenyl)propyl phosphate, trifluoromethyl 3-(3,5-di-n-pentylphenyl)propyl phosphate, trifluoromethyl 3-(2-t-amylphenyl)propyl phosphate, trifluoromethyl 3-(3-t-amylphenyl)propyl phosphate, trifluoromethyl 3-(4-t-amylphenyl)propyl phosphate, trifluoromethyl 3-(2,4-di-t-amylphenyl)propyl phosphate, trifluoromethyl 3-(3,5-di-t-amylphenyl)propyl phosphate, trifluoromethyl 3-(2-cyclopentylphenyl)propyl phosphate, trifluoromethyl 3-(3-cyclopentylphenyl)propyl phosphate, trifluoromethyl 3-(4-cyclopentylphenyl)propyl phosphate, trifluoromethyl 3-(2-cyclohexylphenyl)propyl phosphate, trifluoromethyl 3-(3-cyclohexylphenyl)propyl phosphate, and trifluoromethyl 3-(4-cyclohexylphenyl)propyl phosphate.

From the standpoints of improving safety during overcharge and improving high-temperature storability, preferred examples of the compound represented by general formula (I), among the compounds shown above, are the compounds represented by formulae (a) to (c) in which $R^{13}$ to $R^{16}$ are each independently an alkyl group having 1-3 carbon atoms, a phenyl group, or an aralkyl group and Ar is a phenyl group. Preferred of these are the compounds in which the phenyl groups have no substituent or have one or more secondary or tertiary alkyl groups having 4 or more carbon atoms as substituents. It is also preferable that m should be an integer of 3-5.

In particular, it is more preferable that $R^{13}$ to $R^{16}$ in formulae (a) to (c) should be each independently a methyl, ethyl, phenyl, or 3-phenylpropyl group, and that Ar should be a phenyl group. It is even more preferable that the phenyl groups should have no substituent or have one or more t-butyl, t-amyl, cyclopentyl, or cyclohexyl groups as substituents. It is also more preferable that m should be an integer of 3-5.

It is even more preferable that $R^{13}$ to $R^{16}$ in formulae (a) to (c) should be each independently a methyl, ethyl, or 3-phenylpropyl group, and that Ar should be a phenyl group. It is especially preferable that the phenyl groups should have no substituent or have one or more t-amyl, cyclopentyl, or cyclohexyl groups as substituents. It is even more preferable that m should be an integer of 3-5.

It is especially preferable that $R^{13}$ to $R^{16}$ in formulae (a) to (c) should be each independently a methyl, ethyl, or 3-phenylpropyl group, and it is more preferable that Ar should be a phenyl group. It is especially preferable that the phenyl groups should have no substituent. It is also especially preferable that m should be an integer of 3-5.

Although X in general formula (I) represents an alkoxycarbonyloxy group, organic sulfonate group, or phosphoric acid ester group as stated above, X preferably is an alkoxycarbonyloxy group or an organic sulfonate group, and more preferably is an alkoxycarbonyloxy group.

One of those compounds represented by general formula (I) may be used alone, or two or more thereof may be used in combination.

The proportion of the compound represented by general formula (I) to the nonaqueous electrolytic solution is preferably 0.001% by mass or higher, more preferably 0.01% by mass or higher, even more preferably 0.05% by mass or higher, especially preferably 0.1% by mass or higher. Concentrations thereof lower than the lower limit may result in cases where the effects of the invention are difficult to produce. Conversely, too high concentrations thereof may result in cases where battery capacity decreases. Consequently, the concentration of the compound is preferably 10% by mass or less, more preferably 8% by mass or less, even more preferably 5% by mass or less, especially preferably 3% by mass or less, most preferably 2% by mass or less.

The reasons why the nonaqueous electrolytic solution containing a compound represented by general formula (I) is excellent in terms of safety during overcharge and also in terms of high-temperature storability are unclear. However, these effects are presumed to be brought about by the following mechanism, although the invention should not be construed as being limited by the following.

The compound represented by general formula (I) has in the molecule both Ar (aryl group) to which an alkyl chain having not less than a certain length has been bonded (hereinafter, this aryl group is sometimes referred to as "alkyl-substituted aryl group") and the ester bond in X bonded to the alkyl chain.

In general, compounds having an alkyl-substituted aryl group have a lower oxidation potential than compounds having an aryl group substituted with an ester group, because the former compounds have benzyl-position hydrogen atoms, which are susceptible to oxidation, and can react in an early stage in overcharge to heighten the safety during overcharge. Usually, compounds having a low oxidation potential undesirably react at highly active sites of the electrodes even during high-temperature storage to lower the battery characteristics of the battery which has undergone high-temperature storage.

In the invention, however, it is thought that since an ester group has been bonded through not an aryl group but an alkyl group, the unshared electron pair of the ether oxygen within the ester group stabilizes the benzyl-position carbon atom within the molecule to inhibit side reactions from occurring on the electrodes. Furthermore, in case where m in general formula (I) is 1 and where an ester group has been bonded through an alkyl chain not longer than a given length, the effect is not obtained. It is therefore thought that the intramolecular distance between the aryl group and the ester group is important. Kinetic factors are governing factors in high-temperature storage tests, while thermodynamic factors are governing in overcharge. Consequently, it is presumed that the stabilizing effect of the ether oxygen does not adversely affect the reaction which occurs during overcharge.

In particular, by using the compound in which the Ar (aryl) group has been bonded to the ester group through an alkyl group wherein m is 2 or larger, that is, through an alkyl group having 2 or more carbon atoms, the stabilizing effect of the ether oxygen is enhanced and side reactions with highly active positive electrodes can be inhibited further. It is thus thought that this compound is highly effective in inhibiting battery characteristics from decreasing through high-temperature storage, while heightening safety during overcharge.

(Compound Represented by General Formula (II))

In general formula (II), $R^3$ to $R^{12}$ each independently represent a hydrogen atom, a halogen atom, an optionally substituted hydrocarbon group having 1-12 carbon atoms, an alkoxy group, an alkoxycarbonyloxy group, an organic sulfonate group, or a phosphoric acid ester group, at least one of the $R^3$ to $R^{12}$ representing an alkoxycarbonyloxy group, an organic sulfonate group, or a phosphoric acid ester group.

Examples of the halogen atom include chlorine, fluorine, bromine, and iodine atoms. Preferred are chlorine and fluorine atoms. More preferred is a fluorine atom.

Examples of the optionally substituted hydrocarbon group having 1-12 carbon atoms include alkyl groups having 1-12 carbon atoms, alkenyl groups having 2-12 carbon atoms, aryl groups having 6-12 carbon atoms, or aralkyl groups having 7-12 carbon atoms.

Examples of the alkyl groups having 1-12 carbon atoms include methyl, ethyl, n-propyl, isopropyl, n-butyl, isobutyl, sec-butyl, t-butyl, n-pentyl, t-amyl, n-hexyl, 1,1-dimethylbutyl, cyclobutyl, cyclopentyl, cyclohexyl, 1-methylcyclohexyl, and 1-ethylcyclohexyl. Preferred examples among these, from the standpoint of solubility in the electrolytic solution, include chain or cyclic alkyl groups having preferably 1-6 carbon atoms, more preferably 1-4 carbon atoms, even more preferably 1 or 2 carbon atoms.

Examples of the alkenyl groups having 2-12 carbon atoms include vinyl and propenyl. Preferred examples thereof, from the standpoint of solubility in the electrolytic solution, include alkenyl groups preferably having 2-8 carbon atoms, especially preferably having 2-4 carbon atoms.

Examples of the aryl groups having 6-12 carbon atoms include phenyl, tolyl, xylyl, cyclohexylphenyl, and t-butylphenyl. Preferred of these are phenyl, cyclohexylphenyl, and t-butylphenyl, from the standpoint of oxidation/reduction stability within batteries.

Examples of the aralkyl groups having 7-12 carbon atoms include benzyl, phenethyl, phenylpropyl, phenylbutyl, and phenylpentyl. From the standpoint of improving overcharge characteristics, phenethyl, phenylpropyl, and phenylbutyl are preferred of those, and phenylpropyl is most preferred.

Those alkyl groups, alkenyl groups, aryl groups, and aralkyl groups may have been substituted with one or more fluorine atoms. Examples of the fluorine-substituted groups include fluoroalkyl groups such as trifluoromethyl, trifluoroethyl, and pentafluoroethyl, fluoroalkenyl groups such as 2-fluorovinyl and 3-fluoro-2-propenyl, fluoroaryl groups such as 2-fluorophenyl, 3-fluorophenyl, and 4-fluorophenyl, and fluoroaralkyl groups such as fluorophenylpropyl.

Examples of the alkoxy group include chain alkoxy groups and cyclic alkoxy groups. Preferred of these are a methylalkoxy group, ethylalkoxy group, or phenylalkoxy group, from the standpoint of oxidation/reduction stability within batteries.

Examples thereof include methoxy, ethoxy, n-propoxy, isopropoxy, n-butoxy, isobutoxy, sec-butoxy, t-butoxy, n-pentoxy, t-pentoxy, n-hexyloxy, 1,1-dimethylbutoxy, cyclobutoxy, cyclopentoxy, cyclohexyloxy, 1-methylcyclohexyloxy, 1-ethylcyclohexyloxy, phenoxy, tolyloxy, xylyloxy, cyclohexylphenoxy, and t-butylphenoxy.

The number of carbon atoms of the alkoxy group is usually 1 or larger, and is usually 12 or less, preferably 6 or less, more preferably 4 or less, even more preferably 2 or less.

The alkoxycarbonyloxy group, organic sulfonate group, and phosphoric acid ester group are not particularly limited so long as the groups respectively have the structures of the following formulae (a) to (c). Any desired one of these groups can be used.

[Chem. 5]

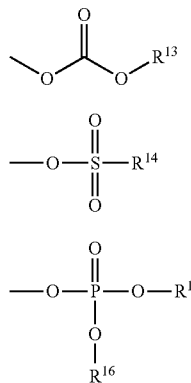

In formulae (a) to (c), $R^{13}$ to $R^{16}$ are the same as in the formulae (a) to (c) explained above in detail with regard to X contained in general formula (I), and preferred modes thereof are also the same.

In the compound represented by formula (II), at least one of $R^3$ to $R^{12}$ is an alkoxycarbonyloxy group, an organic sulfonate group, or a phosphoric acid ester group, preferably an alkoxycarbonyloxy group or an organic sulfonate group, more preferably an alkoxycarbonyloxy group.

In general formula (II), examples of the divalent substituent represented by A, which may contain a heteroatom, include an oxygen atom, sulfur atom, carbonyl, sulfonyl, optionally substituted alkylidene groups, cycloalkylidene groups, arylene groups, arylidene groups, and aralkylidene groups.

Examples of the alkylidene groups or cycloalkylidene groups include methylene, ethylidene, methylmethylene, propylidene, dimethylmethylene, butylidene, methyl-ethyl-methylene, pentylidene, dimethylmethyl-methyl-methylene, hexylidene, dimethylethyl-methyl-methylene, heptylidene, octylidene, nonanylidene, decanylidene, cyclopentylidene, cyclohexylidene, 3-methylcyclohexylidene, 3-isopropylcyclohexylidene, 3-dimethyl-5-methylcyclohexylidene, and a bisdimethylindane group. The alkylidene groups may have been substituted with one or more halogen atoms such as fluorine atoms, and examples thereof include difluoromethylene and ditrifluoromethylmethylene.

Examples of the arylene groups, arylidene groups, or aralkylidene groups include phenylene, phenylidene, phenylmethylene, methylphenylmethylene, diphenylmethylene, biphenylylmethylene, 1,4-phenylenebis(1-methylethylidene), 1,3-phenylenebis(1-methylethylidene), fluorophenylmethylene, fluorene-ylidene, and methoxyphenylmethylene.

From the standpoint of solubility in the electrolytic solution, the number of carbon atoms of the optionally substituted alkylidene group, cycloalkylidene group, arylene group, arylidene group, or aralkylidene group is usually 1 or larger, and is usually 13 or less, preferably 8 or less, more preferably 4 or less.

From the standpoints of improving safety during overcharge and improving high-temperature storability, it is preferable that A in general formula (II) should be an oxygen atom, carbonyl group, sulfonyl group, methylene group, ethylidene group, cyclohexylidene group, 3-dimethyl-5-methylcyclohexylidene group, dimethylmethylene group, or phenylene group, among those examples. More preferably, A is an oxygen atom, carbonyl group, sulfonyl group, cyclohexylidene group, 3-dimethyl-5-methylcyclohexylidene group, dimethylmethylene group, or phenylene group. Even more preferably, A is an oxygen atom, sulfonyl group, cyclohexylidene group, 3-dimethyl-5-methylcyclohexylidene group, dimethylmethylene group, or phenylene group. Most preferably, A is a sulfonyl group, cyclohexylidene group, 3-dimethyl-5-methylcyclohexylidene group, dimethylmethylene group, or phenylene group.

Specific examples of the compound represented by general formula (II) include the following compounds.

Compounds in which at least one of $R^3$ to $R^{12}$ is an alkoxycarbonyloxy group, such as 2,2-bis(p-methoxycarbonyloxyphenyl)propane, 1,1-bis(p-methoxycarbonyloxyphenyl)cyclohexane, bis(p-methoxycarbonyloxyphenyl) sulfone, 2,2-bis(p-methoxycarbonyloxyphenyl)-1,1,1,3,3,3-hexafluoropropane, 2,2-bis(p-methoxycarbonyloxyphenyl)-3-phenylethane, 2,2-bis(p-methoxycarbonyloxyphenyl)butane, 2,2-bis(p-methoxycarbonyloxyphenyl)-1,3-diphenylmethane, 2,2-bis(p-methoxycarbonyloxy-m-methylphenyl)propane, 2,2-bis(p-methoxycarbonyloxy-m-isopropylphenyl)propane, 2,2-bis(p-methoxycarbonyloxyphenyl)propane, 1,4-bis(p-methoxycarbonyloxyphenyl-(1-methylethylidene)benzene, 1,3-bis(p-methoxycarbonyloxyphenyl-(1-methylethylidene)benzene, 2,2-bis(p-methoxycarbonyloxy-m-phenylphenyl)propane, 1,1-bis(p-methoxycarbonyloxyphenyl)-3,3-dimethyl-5-methylcyclohexane, 2,2-bis(p-ethoxycarbonyloxyphenyl)propane, 1,1-bis(p-ethoxycarbonyloxyphenyl)cyclohexane, bis(p-ethoxycarbonyloxyphenyl)sulfone, 2,2-bis(p-ethoxycarbonyloxyphenyl)-1,1,1,3,3,3-hexafluoropropane, 2,2-bis(p-ethoxycarbonyloxyphenyl)-3-phenylethane, 2,2-bis(p-ethoxycarbonyloxyphenyl)butane, 2,2-bis(p-ethoxycarbonyloxyphenyl)-1,3-diphenylmethane, 2,2-bis(p-ethoxycarbonyloxy-m-methylphenyl)propane, 2,2-bis(p-ethoxycarbonyloxy-m-isopropylphenyl)propane, 2,2-bis(p-ethoxycarbonyloxyphenyl)propane, 1,4-bis(p-ethoxycarbonyloxyphenyl-(1-methylethylidene)benzene, 1,3-bis(p-ethoxycarbonyloxyphenyl-(1-methylethylidene)benzene, 2,2-bis(p-ethoxycarbonyloxy-m-phenylphenyl)propane, 1,1-bis(p-ethoxycarbonyloxyphenyl)-3,3-dimethyl-5-methylcyclohexane, 2,2-bis(p-phenoxycarbonyloxyphenyl)propane, 1,1-bis(p-phenoxycarbonyloxyphenyl)cyclohexane, bis(p-phenoxycarbonyloxyphenyl) sulfone, 2,2-bis(p-phenoxycarbonyloxyphenyl)-1,1,1,3,3,3-hexafluoropropane, 2,2-bis(p-phenoxycarbonyloxyphenyl)-3-phenylethane, 2,2-bis(p-phenoxycarbonyloxyphenyl)butane, 2,2-bis(p-phenoxycarbonyloxyphenyl)-1,3-diphenylmethane, 2,2-bis(p-phenoxycarbonyloxy-m-methylphenyl)propane, 2,2-bis(p-phenoxycarbonyloxy-m-isopropylphenyl)propane, 2,2-bis(p-phenoxycarbonyloxyphenyl)propane, 1,4-bis(p- phenoxycarbonyloxyphenyl-(1-methylethylidene)benzene, 1,3-bis(p-phenoxycarbonyloxyphenyl-(1-methylethylidene) benzene, 2,2-bis(p-phenoxycarbonyloxy-m-phenylphenyl) propane, and 1,1-bis(p-phenoxycarbonyloxyphenyl)-3,3-dimethyl-5-methylcyclohexane;

compounds in which at least one of $R^3$ to $R^{12}$ is an organic sulfonate group, such as 2,2-bis(p-methoxysulfonyloxyphenyl)propane, 1,1-bis(p-methoxysulfonyloxyphenyl)cyclohexane, bis(p-methoxysulfonyloxyphenyl) sulfone, 2,2-bis(p-methoxysulfonyloxyphenyl)-1,1,1,3,3,3-hexafluoropropane, 2,2-bis(p-methoxysulfonyloxyphenyl)-3-phenylethane, 2,2-bis(p-methoxysulfonyloxyphenyl)butane, 2,2-bis(p-methoxysulfonyloxyphenyl)-1,3-diphenylmethane, 2,2-bis(p-methoxysulfonyloxy-m-methylphenyl)propane, 2,2-bis(p-methoxysulfonyloxy-m-isopropylphenyl)propane, 2,2-bis(p-methoxysulfonyloxyphenyl)propane, 1,4-bis(p-methoxysulfonyloxyphenyl-(1-methylethylidene)benzene, 1,3-bis(p-methoxysulfonyloxyphenyl-(1-methylethylidene)benzene, 2,2-bis(p-methoxysulfonyloxy-m-phenylphenyl) propane, 1,1-bis(p-methoxysulfonyloxyphenyl)-3,3-dimethyl-5-methylcyclohexane, 2,2-bis(p-ethoxysulfonyloxyphenyl)propane, 1,1-bis(p-ethoxysulfonyloxyphenyl)cyclohexane, bis(p-ethoxysulfonyloxyphenyl) sulfone, 2,2-bis(p-ethoxysulfonyloxyphenyl)-1,1,1,3,3,3-hexafluoropropane, 2,2-bis(p-ethoxysulfonyloxyphenyl)-3-phenylethane, 2,2-bis(p-ethoxysulfonyloxyphenyl)butane, 2,2-bis(p-ethoxysulfonyloxyphenyl)-1,3-diphenylmethane, 2,2-bis(p-ethoxysulfonyloxy-m-methylphenyl)propane, 2,2-bis(p-ethoxysulfonyloxy-m-isopropylphenyl)propane, 2,2-bis(p-ethoxysulfonyloxyphenyl)propane, 1,4-bis(p-ethoxysulfonyloxyphenyl-(1-methylethylidene)benzene, 1,3-bis(p-ethoxysulfonyloxyphenyl-(1-methylethylidene)benzene, 2,2-bis(p-ethoxysulfonyloxy-m-phenylphenyl) propane, 1,1-bis(p-ethoxysulfonyloxyphenyl)-3,3-dimethyl-5-methylcyclohexane, 2,2-bis(p-phenoxysulfonyloxyphenyl)propane, 1,1-bis(p-phenoxysulfonyloxyphenyl)cyclohexane, bis(p-phenoxysulfonyloxyphenyl) sulfone, 2,2-bis(p-phenoxysulfonyloxyphenyl)-1,1,1,3,3,3-hexafluoropropane, 2,2-bis(p-phenoxysulfonyloxyphenyl)-3-phenylethane, 2,2-bis(p-phenoxysulfonyloxyphenyl)butane, 2,2-bis(p-phenoxysulfonyloxyphenyl)-1,3-diphenylmethane, 2,2-bis(p-phenoxysulfonyloxy-m-methylphenyl)propane, 2,2-bis(p-phenoxysulfonyloxy-m-isopropylphenyl)propane, 2,2-bis(p-phenoxysulfonyloxyphenyl)propane, 1,4-bis(p-phenoxysulfonyloxyphenyl-(1-methylethylidene)benzene, 1,3-bis(p-phenoxysulfonyloxyphenyl-(1-methylethylidene)benzene, 2,2-bis(p-phenoxysulfonyloxy-m-phenylphenyl) propane, and 1,1-bis(p-phenoxysulfonyloxyphenyl)-3,3-dimethyl-5-methylcyclohexane; and compounds in which at least one of $R^3$ to $R^{12}$ is a phosphoric acid ester group, such as 2,2-bis(p-methoxydimethoxyphosphorylphenyl)propane, 1,1-bis(p-methoxydimethoxyphosphorylphenyl)cyclohexane, bis(p-methoxydimethoxyphosphorylphenyl) sulfone, 2,2-bis(p-methoxydimethoxyphosphorylphenyl)-1,1,1,3,3,3-hexafluoropropane, 2,2-bis(p-methoxydimethoxyphosphorylphenyl)-3-phenylethane, 2,2-bis(p-methoxydimethoxyphosphorylphenyl)butane, 2,2-bis(p-methoxydimethoxyphosphorylphenyl)-1,3-diphenylmethane, 2,2-bis(p-methoxydimethoxyphosphoryl-m-methylphenyl)propane, 2,2-bis(p-methoxydimethoxyphosphoryl-m-isopropylphenyl)propane, 2,2-bis(p-methoxydimethoxyphosphorylphenyl)propane, 1,4-bis(p-methoxydimethoxyphosphorylphenyl-(1-methylethylidene)benzene, 1,3-bis(p-methoxydimethoxyphosphorylphenyl-(1-methylethylidene)benzene, 2,2-bis(p-methoxydimethoxyphosphoryl-m-phenylphenyl)propane, 1,1-bis(p-methoxydimethoxyphosphorylphenyl)-3,3-dimethyl-5-methylcyclohexane, 2,2-bis(p-ethoxydimethoxyphosphorylphenyl)propane, 1,1-bis(p-ethoxydimethoxyphosphorylphenyl)cyclohexane, bis(p-ethoxydimethoxyphosphorylphenyl) sulfone, 2,2-bis(p-ethoxydimethoxyphosphorylphenyl)-1,1,1,3,3,3-hexafluoropropane, 2,2-bis(p-ethoxydimethoxyphosphorylphenyl)-3-phenylethane, 2,2-bis(p-ethoxydimethoxyphosphorylphenyl)butane, 2,2-bis(p-ethoxydimethoxyphosphorylphenyl)-1,3-diphenylmethane, 2,2-bis(p-ethoxydimethoxyphosphoryl-m-methylphenyl) propane, 2,2-bis(p-ethoxydimethoxyphosphoryl-m-isopropylphenyl)propane, 2,2-bis(p-ethoxydimethoxyphosphorylphenyl)propane, 1,4-bis(p-ethoxydimethoxyphosphorylphenyl-(1-methylethylidene)benzene, 1,3-bis(p-ethoxydimethoxyphosphorylphenyl-(1-methylethylidene)benzene, 2,2-bis(p-ethoxydimethoxyphosphoryl-m-phenylphenyl)propane, 1,1-bis(p-ethoxydimethoxyphosphorylphenyl)-3,3-dimethyl-5-methylcyclohexane, 2,2-bis(p-phenoxydimethoxyphosphorylphenyl)propane, 1,1-bis(p-phenoxydimethoxyphosphorylphenyl)cyclohexane, bis(p-phenoxydimethoxyphosphorylphenyl) sulfone, 2,2-bis(p-phenoxydimethoxyphosphorylphenyl)-1,1,1,3,3,3-hexafluoropropane, 2,2-bis(p-phenoxydimethoxyphosphorylphenyl)-3-phenylethane, 2,2-bis(p-phenoxydimethoxyphosphorylphenyl)butane, 2,2-bis(p-phenoxydimethoxyphosphorylphenyl)-1,3-diphenylmethane, 2,2-bis(p-phenoxydimethoxyphosphoryl-m-methylphenyl)propane, 2,2-bis(p-phenoxydimethoxyphosphoryl-m-isopropylphenyl)propane, 2,2-bis(p-phenoxydimethoxyphosphorylphenyl)propane, 1,4-bis(p-phenoxydimethoxyphosphorylphenyl-(1-methylethylidene)benzene, 1,3-bis(p-phenoxydimethoxyphosphorylphenyl-(1-methylethylidene)benzene, 2,2-bis(p-phenoxydimethoxyphosphoryl-m-phenylphenyl)propane, and 1,1-bis(p-phenoxydimethoxyphosphorylphenyl)-3,3-dimethyl-5-methylcyclohexane.

Preferred examples of the compound, among these, include the following compounds.

Compounds in which at least one of $R^3$ to $R^{12}$ is an alkoxycarbonyloxy group, such as 2,2-bis(p-methoxycarbonyloxyphenyl)propane, 1,1-bis(p-methoxycarbonyloxyphenyl)cyclohexane, 2,2-bis(p-methoxycarbonyloxyphenyl)-1,1,1,3,3,3-hexafluoropropane, 2,2-bis(p-methoxycarbonyloxyphenyl)-3-phenylethane, 2,2-bis(p-methoxycarbonyloxyphenyl)butane, 2,2-bis(p-methoxycarbonyloxy-m-methylphenyl)propane, 2,2-bis(p-methoxycarbonyloxy-m-isopropylphenyl)propane, 2,2-bis(p-methoxycarbonyloxyphenyl)propane, and 1,1-bis(p-methoxycarbonyloxyphenyl)-3,3-dimethyl-5-methylcyclohexane;

compounds in which at least one of $R^3$ to $R^{12}$ is an alkoxycarbonyloxy group, such as 2,2-bis(p-ethoxycarbonyloxyphenyl)propane, 1,1-bis(p-ethoxycarbonyloxyphenyl)cyclohexane, 2,2-bis(p-ethoxycarbonyloxyphenyl)-1,1,3,3,3-hexafluoropropane, 2,2-bis(p-ethoxycarbonyloxyphenyl)-3-phenylethane, 2,2-bis(p-ethoxycarbonyloxyphenyl)butane, 2,2-bis(p-ethoxycarbonyloxy-m-methylphenyl)propane, 2,2-bis(p-ethoxycarbonyloxy-m-isopropylphenyl)propane, 2,2-bis(p-ethoxycarbonyloxyphenyl)propane, and 1,1-bis(p-ethoxycarbonyloxyphenyl)-3,3-dimethyl-5-methylcyclohexane;

compounds in which at least one of $R^3$ to $R^{12}$ is an alkoxycarbonyloxy group, such as 2,2-bis(p-phenoxycarbonyloxyphenyl)propane, 1,1-bis(p-phenoxycarbonyloxyphenyl)cyclohexane, 2,2-bis(p-phenoxycarbonyloxyphenyl)-1,1,1,3,3,3-hexafluoropropane, 2,2-bis(p-phenoxycarbonyloxyphenyl)-3-phenylethane, 2,2-bis(p-phenoxycarbonyloxyphenyl)butane, 2,2-bis(p-phenoxycarbonyloxy-m-methylphenyl)propane, 2,2-bis(p-phenoxycarbonyloxy-m-isopropylphenyl)propane, 2,2-bis(p-phenoxycarbonyloxyphenyl)propane, and 1,1-bis(p-phenoxycarbonyloxyphenyl)-3,3-dimethyl-5-methylcyclohexane;

compounds in which at least one of $R^3$ to $R^{12}$ is an organic sulfonate group, such as 2,2-bis(p-methoxysulfonyloxyphenyl)propane, 1,1-bis(p-methoxysulfonyloxyphenyl)cyclohexane, 2,2-bis(p-methoxysulfonyloxyphenyl)-1,1,1,3,3,3-hexafluoropropane, 2,2-bis(p-methoxysulfonyloxyphenyl)-3-phenylethane, 2,2-bis(p-methoxysulfonyloxyphenyl)butane, 2,2-bis(p-methoxysulfonyloxy-m-methylphenyl)propane, 2,2-bis(p-methoxysulfonyloxy-m-isopropylphenyl)propane, 2,2-bis(p-methoxysulfonyloxyphenyl)propane, and 1,1-bis(p-methoxysulfonyloxyphenyl)-3,3-dimethyl-5-methylcyclohexane;

compounds in which at least one of $R^3$ to $R^{12}$ is an organic sulfonate group, such as 2,2-bis(p-ethoxysulfonyloxyphenyl)propane, 1,1-bis(p-ethoxysulfonyloxyphenyl)cyclohexane, 2,2-bis(p-ethoxysulfonyloxyphenyl)-1,1,1,3,3,3-hexafluoropropane, 2,2-bis(p-ethoxysulfonyloxyphenyl)-3-phenylethane, 2,2-bis(p-ethoxysulfonyloxyphenyl)butane, 2,2-bis(p-ethoxysulfonyloxy-m-methylphenyl)propane, 2,2-bis(p-ethoxysulfonyloxy-m-isopropylphenyl)propane, 2,2-bis(p-ethoxysulfonyloxyphenyl)propane, and 1,1-bis(p-ethoxysulfonyloxyphenyl)-3,3-dimethyl-5-methylcyclohexane; and compounds in which at least one of $R^3$ to $R^{12}$ is an organic sulfonate group, such as 2,2-bis(p-phenoxysulfonyloxyphenyl)propane, 1,1-bis(p-phenoxysulfonyloxyphenyl)cyclohexane, 2,2-bis(p-phenoxysulfonyloxyphenyl)-1,1,1,3,3,3-hexafluoropropane, 2,2-bis(p-phenoxysulfonyloxyphenyl)-3-phenylethane, 2,2-bis(p-phenoxysulfonyloxyphenyl)butane, 2,2-bis(p-phenoxysulfonyloxy-m-methylphenyl)propane, 2,2-bis(p-phenoxysulfonyloxy-m-isopropylphenyl)propane, 2,2-bis(p-phenoxysulfonyloxyphenyl)propane, and 1,1-bis(p-phenoxysulfonyloxyphenyl)-3,3-dimethyl-5-methyl cyclohexane.

More preferred examples of the compound include the following compounds.

Compounds in which at least one of $R^3$ to $R^{12}$ is an alkoxycarbonyloxy group, such as 2,2-bis(p-methoxycarbonyloxyphenyl)propane, 1,1-bis(p-methoxycarbonyloxyphenyl)cyclohexane, 1,1-bis(p-methoxycarbonyloxyphenyl)-3,3,-dimethyl-5-methylcyclohexane, 2,2-bis(p-ethoxycarbonyloxyphenyl)propane, 1,1-bis(p-ethoxycarbonyloxyphenyl)cyclohexane, 1,1-bis(p-ethoxycarbonyloxyphenyl)-3,3,-dimethyl-5-methylcyclohexane, 2,2-bis(p-phenoxycarbonyloxyphenyl)propane, 1,1-bis(p-phenoxycarbonyloxyphenyl)cyclohexane, and 1,1-bis(p-phenoxycarbonyloxyphenyl)-3,3,-dimethyl-5-methylcyclohexane; and compounds in which at least one of $R^3$ to $R^{12}$ is an organic sulfonate group, such as 2,2-bis(p-methoxysulfonyloxyphenyl)propane, 1,1-bis(p-methoxysulfonyloxyphenyl)cyclohexane, 1,1-bis(p-methoxysulfonyloxyphenyl)-3,3,-dimethyl-5-methylcyclohexane, 2,2-bis(p-ethoxysulfonyloxyphenyl)propane, 1,1-bis(p-ethoxysulfonyloxyphenyl)cyclohexane, 1,1-bis(p-ethoxysulfonyloxyphenyl)-3,3,-dimethyl-5-methylcyclohexane, 2,2-bis(p-phenoxysulfonyloxyphenyl)propane, 1,1-bis(p-phenoxysulfonyloxyphenyl)cyclohexane, and 1,1-bis(p-phenoxysulfonyloxyphenyl)-3,3-dimethyl-5-methyl cyclohexane.

One of those compounds represented by general formula (II) may be used alone, or two or more thereof may be used in combination. The proportion of the compound represented by general formula (II) to the nonaqueous electrolytic solution is usually 0.001% by mass or higher, preferably 0.01% by mass or higher, more preferably 0.05% by mass or higher, even more preferably 0.1% by mass or higher, and is usually 10% by mass or less, preferably 8% by mass or less, more preferably 5% by mass or less, even more preferably 3% by mass or less, especially preferably 2.5% by mass or less.

In cases when the proportion thereof is within that range, the effects of the invention are easily produced and a decrease in battery capacity can be prevented.

The compound represented by general formula (II) is not limited so long as the compound satisfies the requirements shown above. It is, however, desirable that the compound should have high solubility in the electrolytic solution, from the standpoint of improving the rate characteristics and low-temperature characteristics of batteries. For example, in the case where a test is used in which a compound is mixed at room temperature with a mixture having a general composition of electrolytic solutions obtained by dissolving 1.0-M $LiPF_6$ in a solvent prepared by mixing ethylene carbonate and ethyl methyl carbonate in a volume ratio of 3:7 and the resultant mixture is examined for phase separation, then the compound represented by general formula (II) has a solubility of usually 0.5% by mass or higher, preferably 0.7% by mass or higher, more preferably 1.0% by mass or higher, most preferably 1.5% by mass or higher.

Specific examples of the compound represented by general formula (II) which satisfy the solubility include the following compounds.

Compounds in which at least one of $R^3$ to $R^{12}$ is an alkoxycarbonyloxy group, such as 2,2-bis(p-methoxycarbonyloxyphenyl)propane, 1,1-bis(p-methoxycarbonyloxyphenyl)cyclohexane, 1,1-bis(p-methoxycarbonyloxyphenyl)-3,3,-dimethyl-5-methylcyclohexane, 2,2-bis(p-ethoxycarbonyloxyphenyl)propane, 1,1-bis(p-ethoxycarbonyloxyphenyl)cyclohexane, and 1,1-bis(p-ethoxycarbonyloxyphenyl)-3,3,-dimethyl-5-methylcyclohexane;

compounds in which at least one of $R^3$ to $R^{12}$ is an organic sulfonate group, such as 2,2-bis(p-methoxysulfonyloxyphenyl)propane, 1,1-bis(p-methoxysulfonyloxyphenyl)cyclohexane, 1,1-bis(p-methoxysulfonyloxyphenyl)-3,3,-dimethyl-5-methylcyclohexane, 2,2-bis(p-ethoxysulfonyloxyphenyl)propane, 1,1-bis(p-ethoxysulfonyloxyphenyl)cyclohexane, and 1,1-bis(p-ethoxysulfonyloxyphenyl)-3,3,-dimethyl-5-methylcyclohexane.

The reasons why the nonaqueous electrolytic solution containing a compound represented by general formula (II) is excellent in terms of safety during overcharge and also in terms of high-temperature storability are unclear. However, these effects are presumed to be brought about by the following mechanism, although the invention should not be construed as being limited by the following.

The compound represented by general formula (II) has two benzene rings and a divalent group which connects the two benzene rings to each other, and further has substituents on the benzene rings.

In general, compounds including two or more benzene rings connected to each other have a low oxidation potential and high reactivity due to the conjugation of π-electrons and, hence, can react in an earlier stage in overcharge, than compounds having only one benzene ring, to heighten the safety during overcharge. However, such compounds having conjugation usually have low activation energy in oxidation reactions and undesirably react at highly active sites of the electrodes even during high-temperature storage to lower the battery characteristics of the battery which has undergone high-temperature storage. In addition, since such compounds are prone to be reduced on the negative electrode of the battery, the compounds tend to deteriorate the coating film of the negative electrode. Although the storability is improved by bonding two benzene rings with a divalent group, this structure results also in a decrease in reactivity during overcharge, making it impossible to ensure sufficient safety.

In the invention, however, it is thought that the interposition of a divalent substituent of an appropriate size between the two benzene rings elevates the activation energy for oxidation reactions to inhibit side reactions from occurring on the electrodes during battery durability tests such as high-temperature storage, and that the substituents possessed by the benzene rings enhance the reactivity during overcharge.

It is also presumed that the electron-donating/attracting properties of the divalent substituent which connects the two benzene rings are balanced with those of the substituents on each benzene ring, thereby inhibiting reduction on the negative electrode in the battery and improving storability. Furthermore, the feature wherein at least one of $R^3$ to $R^{12}$ in general formula (II) is any of the three groups, i.e., an alkoxycarbonyloxy group, an organic sulfonate group, and a phosphoric ester group, has the effect of heightening the solubility in the electrolytic solution.

In particular, in the compound in which two benzene rings have been bonded through a divalent substituent and which has one or more substituents on the benzene rings, as in the invention, the effect of stabilizing the benzene rings is high. Consequently, side reactions with the positive electrode, which has high activity, can be inhibited further. Moreover, by suitably setting the properties of the divalent substituent simultaneously therewith, the two benzene rings, which do not react during storage, are made to react when in a high-energy state as in overcharge. It is therefore thought that this compound is highly effective in inhibiting battery characteristics from decreasing through high-temperature storage, while heightening safety during overcharge.

In the case where a compound represented by general formula (I) and a compound represented by general formula (II) are used in combination, the total content of the compound represented by general formula (I) and the compound represented by general formula (II) in the nonaqueous electrolytic solution is usually 0.001% by mass or higher, preferably 0.01% by mass or higher, more preferably 0.1% by mass or higher, and is usually 10% by mass or less, preferably 5% by mass or less, more preferably 3% by mass or less, from the standpoint of the electrical conductivity of the nonaqueous electrolytic solution.

Of the compounds represented by general formula (II), 1,1-bis(p-methoxycarbonyloxyphenyl)cyclohexane, which is represented by the following formula (III), can be synthesized by the following method.

[Chem. 6]

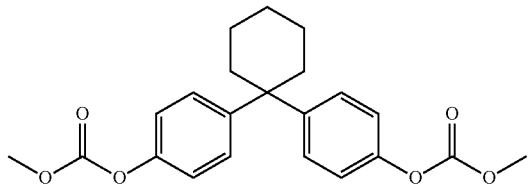

(III)

Bisphenol A, dichloromethane, and triethylamine are mixed together in a nitrogen atmosphere, and methyl chloroformate is added thereto and reacted while cooling the mixture with ice. Thereafter, water is added thereto to thereby terminate the reaction. The resultant liquid reaction mixture is subjected to an extraction operation to obtain an organic layer, and this organic layer is washed and dried. Thus, the compound represented by formula (III) can be obtained. The compound obtained is repeatedly subjected to a recrystallization operation. As a result, the compound having a higher purity can be obtained.

As an extractant for the extraction operation in the synthesis, dichloromethane can, for example, be used. For the washing, use can be made of dilute hydrochloric acid, water, aqueous sodium chloride solution, or the like. For the drying, anhydrous sodium sulfate or the like can be used. As a solvent for the recrystallization, ethyl acetate or the like can be used. However, usable solvents, etc. are not limited to these.

(Electrolyte)

There are no limitations on the electrolyte to be used in the nonaqueous electrolytic solution of the invention, and a known electrolyte can be used at will so long as the electrolyte is for use in desired nonaqueous-electrolyte secondary batteries.

In the case where the nonaqueous electrolytic solution of the invention is for use in lithium secondary batteries, a lithium salt is usually used as the electrolyte.

Examples of the electrolyte include: inorganic lithium salts such as $LiClO_4$, $LiAsF_6$, $LiPF_6$, $LiBF_4$, and $LiFSO_3$; fluorine-containing organic lithium salts such as $LiCF_3SO_3$, $LiN(CF_3SO_2)_2$, $LiN(C_2F_5SO_2)_2$, the lithium salt of cyclic 1,2-tetrafluoroethanedisulfonylimide, the lithium salt of cyclic 1,3-hexafluoropropanedisulfonylimide, $LiN(CF_3SO_2)(C_4F_9SO_2)$, $LiC(CF_3SO_2)_3$, $LiPF_4(CF_3)_2$, $LiPF_4(C_2F_5)_2$, $LiPF_4(CF_3SO_2)_2$, $LiPF_4(C_2F_5SO_2)_2$, $LiBF_2(CF_3)_2$, $LiBF_2(C_2F_5)_2$, $LiBF_2(CF_3SO_2)_2$, and $LiBF_2(C_2F_5SO_2)_2$; and dicarboxylic acid complex lithium salts such as lithium bis(oxalato)borate, lithium difluorooxalatoborate, lithium tris(oxalato)phosphate, lithium difluorobis(oxalato)phosphate, and lithium tetrafluorooxalatophosphate.

Preferred of these are $LiPF_6$, $LiBF_4$, $LiFSO_3$, $LiCF_3SO_3$, $LiN(CF_3SO_2)_2$, $LiN(C_2F_5SO_2)_2$, the lithium salt of cyclic 1,2-tetrafluoroethanedisulfonylimide, the lithium salt of cyclic 1,3-hexafluoropropanedisulfonylimide, lithium bis(oxalato)borate, lithium difluorooxalatoborate, lithium tris(oxalato)phosphate, lithium difluorobis(oxalato)phosphate, and lithium tetrafluorooxalatophosphate. Especially preferred are $LiPF_6$ and $LiBF_4$.

One of these lithium salts may be used alone, or any desired two or more thereof may be used in combination in any desired proportion. Preferred of those lithium salts is a combination of specific inorganic lithium salts or a combination of an inorganic lithium salt with a fluorine-containing organic lithium salt or carboxylic acid complex lithium salt. This is because use of such combination inhibits gas evolution during high-temperature storage or inhibits deterioration through high-temperature storage.

Especially preferred is to use $LiPF_6$ and $LiBF_4$ in combination or to use an inorganic lithium salt, such as $LiPF_6$ or $LiBF_4$, in combination with a fluorine-containing organic lithium salt such as $LiCF_3SO_3$, $LiN(CF_3SO_2)_2$, $LiN(C_2F_5SO_2)_2$, the lithium salt of cyclic 1,2-tetrafluoroethanedisulfonylimide, and the lithium salt of cyclic 1,3-hexafluoropropanedisulfonylimide or with a dicarboxylic acid complex lithium salt such as lithium bis(oxalato)borate, lithium difluorooxalatoborate, lithium tris(oxalato)phosphate, lithium difluorobis(oxalato)phosphate, or lithium tetrafluorooxalatophosphate.

In the case of using $LiPF_6$ and $LiBF_4$ in combination, the proportion of $LiBF_4$ to the sum of $LiPF_6$ and $LiBF_4$ is preferably 0.01% by mass or higher, more preferably 0.05% by mass or higher, even more preferably 0.1% by mass or higher, and is preferably 20% by mass or less, more preferably 10% by mass or less, even more preferably 5% by mass or less, especially preferably 3% by mass or less.

In cases when the proportion thereof is within that range, the desired effects are easy to obtain and battery characteristics including high-load discharge characteristics are prevented from decreasing.

Meanwhile, in the case of using an inorganic lithium salt, such as $LiPF_6$ or $LiBF_4$, in combination with a fluorine-containing organic lithium salt such as $LiCF_3SO_3$, $LiN(CF_3SO_2)_2$, $LiN(C_2F_5SO_2)_2$, the lithium salt of cyclic 1,2-tetrafluoroethanedisulfonylimide, and the lithium salt of cyclic 1,3-hexafluoropropanedisulfonylimide or with a dicarboxylic acid complex lithium salt such as lithium bis(oxalato)borate, lithium difluorooxalatoborate, lithium tris(oxalato)phosphate, lithium difluorobis(oxalato)phosphate, or lithium tetrafluorooxalatophosphate, the proportion of the inorganic lithium salt to the sum of both is preferably 70% by mass or higher, more preferably 80% by mass or higher, even more preferably 85% by mass or higher, and is preferably 99% by mass or less, more preferably 95% by mass or less.

The concentration of these electrolytes in the nonaqueous electrolytic solution is not particularly limited from the standpoint of producing the effects of the invention. However, the concentration thereof is preferably 0.5 mol/L or higher, more preferably 0.8 mol/L or higher, even more preferably 1.0 mol/L or higher, and is preferably 3 mol/L or less, more preferably 2 mol/L or less, even more preferably 1.8 mol/L or less, especially preferably 1.6 mol/L or less.

In cases when the electrolyte concentration is within that range, the electrolytic solution has sufficient electrical conductivity and can be prevented from suffering a decrease in electrical conductivity or battery performance due to an increase in viscosity.

(Nonaqueous Solvent)

With respect to the nonaqueous solvent also, use can be made of a nonaqueous solvent suitably selected from ones which have conventionally been known as solvents for nonaqueous electrolytic solutions.

Examples thereof include cyclic carbonates, chain carbonates, cyclic carboxylic acid esters, chain carboxylic acid esters, cyclic ethers, chain ethers, sulfur-containing organic solvents, phosphorus-containing organic solvents, and fluorine-containing aromatic solvents.

Examples of the cyclic carbonates include alkylene carbonates having an alkylene group with 2-4 carbon atoms, such as ethylene carbonate, propylene carbonate, and butylene carbonate. Of these, ethylene carbonate and propylene carbonate are preferred from the standpoint of improving battery characteristics, and ethylene carbonate is especially preferred. These compounds may be ones in which the hydrogen atoms have been partly replaced with fluorine atoms.

Examples of such cyclic carbonates substituted with one or more fluorine atoms include alkylene carbonates which have an alkylene group having 2-4 carbon atoms and substituted with one or more fluorine atoms, such as fluoroethylene carbonate, 1,2-difluoroethylene carbonate, 1,1-difluoroethylene carbonate, 1,1,2-trifluoroethylene carbonate, tetrafluoroethylene carbonate, 1-fluoro-2-methylethylene carbonate, 1-fluoro-1-methylethylene carbonate, 1,2-difluoro-1-methylethylene carbonate, 1,1,2-trifluoro-2-methylethylene carbonate, and trifluoromethylethylene carbonate. Preferred of these are fluoroethylene carbonate, 1,2-difluoroethylene carbonate, and trifluoromethylethylene carbonate.

Preferred as the chain carbonates are dialkyl carbonates, in each of which the number of carbon atoms of each constituent alkyl group is preferably 1-5, especially preferably 1-4.

Specific examples thereof include: symmetrical chain alkyl carbonates such as dimethyl carbonate, diethyl carbonate, and di-n-propyl carbonate; and unsymmetrical chain alkyl carbonates such as ethyl methyl carbonate, methyl n-propyl carbonate, and ethyl n-propyl carbonate. Preferred of these, from the standpoint of improving battery characteristics, are dimethyl carbonate, diethyl carbonate, and ethyl methyl carbonate.

The hydrogen atoms of the alkyl groups may have been partly replaced with fluorine atoms. Examples of such chain carbonates substituted with one or more fluorine atoms include bis(fluoromethyl) carbonate, bis(difluoromethyl) carbonate, bis(trifluoromethyl) carbonate, bis(2-fluoroethyl) carbonate, bis(2,2-difluoroethyl) carbonate, bis(2,2,2-trifluoroethyl) carbonate, 2-fluoroethyl methyl carbonate, 2,2-difluoroethyl methyl carbonate, and 2,2,2-trifluoroethyl methyl carbonate.

Examples of the cyclic carboxylic acid esters include γ-butyrolactone, γ-valerolactone, and the like and compounds obtained by partly replacing the hydrogen atoms of these compounds with fluorine atoms.

Examples of the chain carboxylic acid esters include compounds such as methyl acetate, ethyl acetate, propyl acetate, isopropyl acetate, butyl acetate, sec-butyl acetate, isobutyl acetate, t-butyl acetate, methyl propionate, ethyl propionate, propyl propionate, isopropyl propionate, methyl butyrate, ethyl butyrate, propyl butyrate, methyl valerate, and ethyl valerate and compounds obtained by partly replacing the hydrogen atoms of these compounds with fluorine atoms, such as propyl trifluoroacetate and butyl trifluoroacetate. More preferred of these are methyl acetate, ethyl acetate, propyl acetate, butyl acetate, methyl propionate, ethyl propionate, propyl propionate, methyl butyrate, ethyl butyrate, and methyl valerate.

Examples of the cyclic ethers include tetrahydrofuran, 2-methyltetrahydrofuran, and the like and compounds obtained by partly replacing the hydrogen atoms of these compounds with fluorine atoms.

Examples of the chain ethers include compounds such as dimethoxyethane and diethoxyethane and compounds obtained by partly replacing the hydrogen atoms of these compound with fluorine atoms, such as bistrifluoroethoxyethane, ethoxytrifluoroethoxyethane, methoxytrifluoroethoxyethane, 1,1,1,2,2,3,4,5,5,5-decafluoro-3-methoxy-4-trifluoromethylpentane, 1,1,1,2,2,3,4,5,5,5-decafluoro-3-ethoxy-4-trifluoromethylpentane, 1,1,1,2,2,3,4,5,5,5-decafluoro-3-propoxy-4-trifluoromethylpentane, 1,1,2,2-tetrafluoroethyl 2,2,3,3-tetrafluoropropyl ether, and 2,2-difluoroethyl 2,2,3,3-tetrafluoropropyl ether.

Examples of the sulfur-containing organic solvents include compounds such as sulfolane, 2-methylsulfolane, 3-methylsulfolane, diethyl sulfone, ethyl methyl sulfone, and methyl propyl sulfone and compounds obtained by partly replacing the hydrogen atoms of these compounds with fluorine atoms.

Examples of the phosphorus-containing organic solvents include trimethyl phosphate, triethyl phosphate, dimethyl ethyl phosphate, methyl diethyl phosphate, ethylene methyl phosphate, ethylene ethyl phosphate, and the like and compounds obtained by partly replacing the hydrogen atoms of these compounds with fluorine atoms.

Examples of the fluorine-containing aromatic solvents include fluorobenzene, difluorobenzene, trifluorobenzene, tetrafluorobenzene, pentafluorobenzene, hexafluorobenzene, and benzotrifluoride.

These compounds may be used either alone or in combination of two or more thereof. It is, however, preferred to use two or more compounds in combination. For example, it is preferred to use a high-permittivity solvent, such as a cyclic carbonate or a cyclic carboxylic acid ester, in combination with a low-viscosity solvent, such as a chain carbonate or a chain carboxylic acid ester.

One preferred combination of nonaqueous-solvent compounds is a combination consisting mainly of an alkylene carbonate and a dialkyl carbonate. Preferred of such combinations is a combination in which the total proportion of the alkylene carbonate and the dialkyl carbonate to the nonaqueous solvent is preferably 70% by volume or higher, more preferably 80% by volume or higher, even more preferably 90% by volume or higher, and in which the proportion of the alkylene carbonate to the sum of the alkylene carbonate and the dialkyl carbonate is preferably 5% by volume or higher, more preferably 10% by volume or higher, even more preferably 15% by volume or higher, and is preferably 50% by volume or less, more preferably 35% by volume or less, even more preferably 30% by volume or less, especially preferably 25% by volume or less.

There are cases where use of such a combination of nonaqueous-solvent compounds results in an improved balance between the cycling characteristics and high-temperature storability (in particular, residual capacity and high-load discharge capacity after high-temperature storage) of the battery produced.

Preferred examples of the alkylene carbonate are ethylene carbonate, propylene carbonate, and fluoroethylene carbonate from the standpoint of improving the cycling characteristics and high-temperature storability of batteries.

Examples of preferred ethylene carbonate/dialkyl carbonate combinations include: ethylene carbonate/dimethyl carbonate; ethylene carbonate/diethyl carbonate; ethylene carbonate/ethyl methyl carbonate; ethylene carbonate/dimethyl carbonate/diethyl carbonate; ethylene carbonate/dimethyl carbonate/ethyl methyl carbonate; ethylene carbonate/diethyl carbonate/ethyl methyl carbonate; and ethylene carbonate/dimethyl carbonate/diethyl carbonate/ethyl methyl carbonate.

Other preferred combinations include combinations obtained by further adding propylene carbonate to those combinations of ethylene carbonate with one or more dialkyl carbonates.

In the case where propylene carbonate is contained, the volume ratio of the ethylene carbonate to the propylene carbonate is preferably 99:1 to 40:60, especially preferably 95:5 to 50:50.

Furthermore, the proportion of the propylene carbonate to the whole nonaqueous solvent is preferably 0.1% by volume or higher, more preferably 1% by volume or higher, even more preferably 2% by volume or higher, and is preferably 20% by volume or less, more preferably 8% by volume or less, even more preferably 5% by volume or less. In cases when propylene carbonate is contained in a concentration within that range, this nonaqueous solvent is preferred since there are cases where the electrolytic solution has even better low-temperature characteristics while retaining the properties brought about by the combination of ethylene carbonate and dialkyl carbonate(s).

More preferred of the combinations of ethylene carbonate with one or more dialkyl carbonates are combinations which include an unsymmetrical chain alkyl carbonate as a dialkyl carbonate. Especially preferred are combinations including ethylene carbonate, a symmetrical chain alkyl carbonate, and an unsymmetrical chain alkyl carbonate, such as ethylene carbonate/dimethyl carbonate/ethyl methyl carbonate, ethylene carbonate/diethyl carbonate/ethyl methyl carbonate, and ethylene carbonate/dimethyl carbonate/diethyl carbonate/ethyl methyl carbonate. This is because a satisfactory balance between cycling characteristics and high-current discharge characteristics is brought about thereby. Preferred of these are the combinations in which the unsymmetrical chain alkyl carbonate is ethyl methyl carbonate. The number of carbon atoms of each alkyl group of the alkyl carbonates is preferably 1 or 2.

Examples of preferred fluoroethylene carbonate/dialkyl carbonate combinations include: fluoroethylene carbonate/dimethyl carbonate; fluoroethylene carbonate/diethyl carbonate; fluoroethylene carbonate/ethyl methyl carbonate; fluoroethylene carbonate/dimethyl carbonate/diethyl carbonate; fluoroethylene carbonate/dimethyl carbonate/ethyl methyl carbonate; fluoroethylene carbonate/diethyl carbonate/ethyl methyl carbonate; and fluoroethylene carbonate/dimethyl carbonate/diethyl carbonate/ethyl methyl carbonate.

Other preferred combinations include combinations obtained by further adding ethylene carbonate and/or propylene carbonate to those combinations of fluoroethylene carbonate with one or more dialkyl carbonates.

In the case where the nonaqueous solvent includes diethyl carbonate, the proportion of the diethyl carbonate to the whole nonaqueous solvent is preferably 10% by volume or higher, more preferably 20% by volume or higher, even more preferably 25% by volume or higher, especially preferably 30% by volume or higher, and is preferably 90% by volume or less, more preferably 80% by volume or less, even more preferably 75% by volume or less, especially preferably 70% by volume or less. There are cases where by incorporating diethyl carbonate in an amount within that range, gas evolution during high-temperature storage is inhibited.

In the case where the nonaqueous solvent includes dimethyl carbonate, the proportion of the dimethyl carbonate to the whole nonaqueous solvent is preferably 10% by volume or higher, more preferably 20% by volume or higher, even more preferably 25% by volume or higher, especially preferably 30% by volume or higher, and is preferably 90% by volume or less, more preferably 80% by volume or less, even more preferably 75% by volume or less, especially preferably 70% by volume or less. There are cases where by incorporating dimethyl carbonate in an amount within that range, the battery has improved load characteristics.

In the case where the nonaqueous electrolytic solution contains a compound represented by general formula (II), it is preferable that this electrolytic solution should contain dimethyl carbonate and ethyl methyl carbonate so that the proportion of the dimethyl carbonate is higher than the proportion of the ethyl methyl carbonate. This is because there are cases where this electrolytic solution enables the battery to show improved characteristics after high-temperature storage, while retaining the electrical conductivity.

The volume ratio of the dimethyl carbonate to the ethyl methyl carbonate (dimethyl carbonate/ethyl methyl carbonate) in the whole nonaqueous solvent is preferably 1.1 or higher, more preferably 1.5 or higher, even more preferably 2.5 or higher, from the standpoints of improving the electrical conductivity of the electrolytic solution and improving the characteristics of the battery which has been stored. The volume ratio thereof (dimethyl carbonate/ethyl methyl carbonate) is preferably 40 or less, more preferably 20 or less, even more preferably 10 or less, especially preferably 8 or less, from the standpoint of improving low-temperature battery characteristics.

In the invention, in the case of a combination consisting mainly of any of the alkylene carbonates and any of the dialkyl carbonates, solvents other than the alkylene carbonates and dialkyl carbonates may be mixed therewith. Examples of the other solvents include cyclic carbonates, chain carbonates, cyclic carboxylic acid esters, chain carboxylic acid esters, cyclic ethers, chain ethers, sulfur-containing organic solvents, phosphorus-containing organic solvents, and fluorine-containing aromatic solvents.

Other preferred examples of the nonaqueous solvent is a nonaqueous solvent in which a mixed solvent composed of one or more organic solvents selected from the group consisting of ethylene carbonate, propylene carbonate, and butylene carbonate accounts for at least 60% by volume of the whole nonaqueous solvent. There are cases where the nonaqueous electrolytic solution employing this mixed solvent is less apt to sulfur solvent vaporization or liquid leakage even when used at high temperatures.

In particular, there are case where use of a nonaqueous solvent in which the total proportion of ethylene carbonate and propylene carbonate to the nonaqueous solvent is preferably 70% by volume or higher, more preferably 80% by volume or higher, even more preferably 90% by volume or higher, and in which the volume ratio of the ethylene carbonate to the propylene carbonate is preferably 30:70 to 60:40 brings about an improved balance between cycling characteristics and high-temperature storability, etc.

In this description, the volumes of nonaqueous solvents are values measured at 25° C. However, for solvents which are solid at 25° C., like ethylene carbonate, values measured at the melting points are used.

(Other Compounds)

The nonaqueous electrolytic solution according to the invention may contain, as aids, at least one compound selected from the group consisting of cyclic carbonate compounds having a carbon-carbon unsaturated bond, cyclic carbonate compounds having a fluorine atom, monofluorophosphoric acid salts, and difluorophosphoric acid salts and other various compounds including conventionally known overcharge inhibitors, so long as the incorporation thereof does not lessen the effects of the invention.

Preferred of such cases is the case where the nonaqueous electrolytic solution contains at least one compound selected from the group consisting of cyclic carbonate compounds having a carbon-carbon unsaturated bond, cyclic carbonate compounds having a fluorine atom, monofluorophosphoric acid salts, and difluorophosphoric acid salts. This is because there are cases where this electrolytic solution forms a stable coating film on the negative electrode to improve cycling characteristics and the characteristics of the battery which has undergone high-temperature storage.

((Cyclic Carbonate Compounds Having Carbon-Carbon Unsaturated Bond))

Examples of the cyclic carbonate compounds having a carbon-carbon unsaturated bond include: vinylene carbonate compounds such as vinylene carbonate, methylvinylene carbonate, ethylvinylene carbonate, 1,2-dimethylvinylene carbonate, 1,2-diethylvinylene carbonate, fluorovinylene carbonate, and trifluoromethylvinylene carbonate; vinylethylene carbonate compounds such as vinylethylene carbonate, 1-methyl-2-vinylethylene carbonate, 1-ethyl-2-vinylethylene carbonate, 1-n-propyl-2-vinylethylene carbonate, 1-methyl-2-vinylethylene carbonate, 1,1-divinylethylene carbonate, and 1,2-divinylethylene carbonate; and methyleneethylene carbonate compounds such as 1,1-dimethyl-2-methyleneethylene carbonate and 1,1-diethyl-2-methyleneethylene carbonate.

Preferred of these are vinylene carbonate, vinylethylene carbonate, and 1,2-divinylethylene carbonate, from the standpoint of improving cycling characteristics and capacity retentivity after high-temperature storage. More preferred of these is vinylene carbonate or vinylethylene carbonate. Especially preferred is vinylene carbonate.

These compounds may be used either alone or in combination of two or more thereof. In the case where two or more compounds are used in combination, it is preferred to use vinylene carbonate and vinylethylene carbonate in combination.

((Cyclic Carbonate Compounds Having Fluorine Atom))

Examples of the cyclic carbonate compounds having a fluorine atom include fluoroethylene carbonate, 1,2-difluoroethylene carbonate, 1,1-difluoroethylene carbonate, 1,1,2-trifluoroethylene carbonate, tetrafluoroethylene carbonate, 1-fluoro-2-methylethylene carbonate, 1-fluoro-1-methylethylene carbonate, 1,2-difluoro-1-methylethylene carbonate, 1,1,2-trifluoro-2-methylethylene carbonate, and trifluoromethylethylene carbonate.

Preferred of these are fluoroethylene carbonate, 1,2-difluoroethylene carbonate, and 1-fluoro-2-methylethylene carbonate, from the standpoints of improving cycling characteristics and improving high-temperature storability. These compounds may be used either alone or in combination of two or more thereof.

These compounds may be used also in combination with any of the cyclic carbonate compounds having a carbon-carbon unsaturated bond or with any of the monofluorophosphoric acid salts and difluorophosphoric acid salts described below. Such a combination is preferred from the standpoints of improving cycling characteristics and improving high-temperature storability.

((Monofluorophosphoric Acid Salts and Difluorophosphoric Acid Salts))

The monofluorophosphoric acid salts and the difluorophosphoric acid salts are not particularly limited in the counter cations thereof. Examples of the counter cations include lithium, sodium, potassium, magnesium, calcium, or ammoniums represented by $NR^{21}R^{22}R^{23}R^{24}$ (wherein $R^{21}$ to $R^{24}$ each independently represent a hydrogen atom or an organic group having 1-12 carbon atoms).

The organic groups having 1-12 carbon atoms represented by $R^{21}$ to $R^{24}$ in the ammoniums are not particularly limited. Examples thereof include alkyl groups which may be substituted with one or more halogen atoms, cycloalkyl groups which may be substituted with one or more halogen atoms or alkyl groups, aryl groups which may be substituted with one or more halogen atoms or alkyl groups, and nitrogen-atom-containing heterocyclic groups which may have one or more substituents. In particular, it is preferable that $R^{21}$ to $R^{24}$ should be each independently a hydrogen atom, alkyl group, cycloalkyl group, nitrogen-atom-containing heterocyclic group, or the like.

Examples of the monofluorophosphoric acid salts and difluorophosphoric acid salts include lithium monofluorophosphate, sodium monofluorophosphate, potassium monofluorophosphate, tetramethylammonium monofluorophosphate, tetraethylammonium monofluorophosphate, lithium difluorophosphate, sodium difluorophosphate, potassium difluorophosphate, tetramethylammonium difluorophosphate, and tetraethylammonium difluorophosphate. Preferred are lithium monofluorophosphate and lithium difluorophosphate. More preferred is lithium difluorophosphate.

These compounds may be used either alone or in combination of two or more thereof.

These compounds may be used also in combination with any of the cyclic carbonate compounds having a carbon-carbon unsaturated bond or with any of the cyclic carbonate compounds having a fluorine atom. Such a combination is preferred from the standpoints of improving cycling characteristics and improving the characteristics of the battery which has undergone high-temperature storage.

In the case where the nonaqueous electrolytic solution contains a cyclic carbonate compound having a carbon-carbon unsaturated bond, the proportion thereof in the nonaqueous electrolytic solution is preferably 0.001% by mass or higher, more preferably 0.01% by mass or higher, even more preferably 0.1% by mass or higher, especially preferably 0.3% by mass or higher, and is preferably 8% by mass or less, more preferably 4% by mass or less, even more preferably 3% by mass or less.

In cases when the proportion of the cyclic carbonate compound having a carbon-carbon unsaturated bond is within that range, not only the effect of improving both the cyclic characteristics of batteries and the capacity retentivity thereof after high-temperature storage can be sufficiently exhibited, but also gas evolution is prevented from increasing during high-temperature storage and discharge characteristics are prevented from decreasing at low temperatures.

In the case where the nonaqueous electrolytic solution contains as an aid a cyclic carbonate compound having a fluorine atom, the proportion of this aid in the nonaqueous electrolytic solution is preferably 0.001% by mass or higher, more preferably 0.1% by mass or higher, even more preferably 0.3% by mass or higher, especially preferably 0.5% by mass or higher, and is preferably 10% by mass or less, more preferably 5% by mass or less, even more preferably 4% by mass or less, especially preferably 3% by mass or less.

In cases when the proportion of the cyclic carbonate compound having a fluorine atom is within that range, not only the effect of improving the cycling characteristics and high-temperature storability of batteries can be sufficiently exhibited, but also gas evolution can be prevented from increasing during high-temperature storage and discharge characteristics can be prevented from decreasing at low temperatures.

In the case where the nonaqueous electrolytic solution contains a monofluorophosphoric acid salt and/or a difluorophosphoric acid salt, the proportion thereof in the nonaqueous electrolytic solution is preferably 0.001% by mass or higher, more preferably 0.01% by mass or higher, even more preferably 0.1% by mass or higher, especially preferably 0.2% by mass or higher, and is preferably 5% by mass or less, more preferably 3% by mass or less, even more preferably 2% by mass or less.

In cases when the proportion of the monofluorophosphoric acid salt and/or difluorophosphoric acid salt is within that range, the effect of improving the cycling characteristics and high-temperature storability of batteries can be sufficiently exhibited. In addition, the salt(s) can be prevented from becoming difficult to dissolve in the electrolytic solution, and the tendency that the effect becomes unable to be enhanced any more can be avoided.

Examples of the conventionally known overcharge inhibitors include: aromatic compounds such as biphenyl, alkylbiphenyls, e.g., 2-methylbiphenyl and 2-ethylbiphenyl, terphenyl, partly hydrogenated terphenyls, cyclopentylbenzene, cyclohexylbenzene, cis-1-propyl-4-phenylcyclohexane, trans-1-propyl-4-phenylcyclohexane, cis-1-butyl-4-phenylcyclohexane, trans-1-butyl-4-phenylcyclohexane, toluene, ethylbenzene, t-butylbenzene, t-amylbenzene, diphenyl ether, dibenzofuran, methyl phenyl carbonate, ethyl phenyl carbonate, diphenyl carbonate, methyl phenyl sulfonate, ethyl phenyl sulfonate, diphenyl sulfonate, triphenyl phosphate, tris(2-t-butylphenyl)phosphate, tris(3-t-butylphenyl)phosphate, tris(4-t-butylphenyl)phosphate, tris(2-t-amylphenyl)phosphate, tris(3-t-amylphenyl)phosphate, tris(4-t-amylphenyl)phosphate, tris(2-cyclohexylphenyl)phosphate, tris(3-cyclohexylphenyl)phosphate, and tris(4-cyclohexylphenyl)phosphate; compounds obtained by partly fluorinating these aromatic compounds, such as 2-fluorobiphenyl, 3-fluorobiphenyl, 4-fluorobiphenyl, 4,4'-difluorobiphenyl, 2,4-difluorobiphenyl, o-cyclohexylfluorobenzene, and p-cyclohexylfluorobenzene; and fluorine-containing anisole compounds such as 2,4-difluoroanisole, 2,5-difluoroanisole, 2,6-difluoroanisole, and 3,5-difluoroanisole.

Preferred of these are: aromatic compounds such as biphenyl, alkylbiphenyls, e.g., 2-methylbiphenyl, terphenyl, partly hydrogenated terphenyls, cyclopentylbenzene, cyclohexylbenzene, cis-1-propyl-4-phenylcyclohexane, trans-1-propyl-4-phenylcyclohexane, cis-1-butyl-4-phenylcyclohexane, trans-1-butyl-4-phenylcyclohexane, toluene, ethylbenzene, t-butylbenzene, t-amylbenzene, diphenyl ether, dibenzofuran, methyl phenyl carbonate, diphenyl carbonate, methyl phenyl sulfonate, diphenyl sulfonate, triphenyl phosphate, tris(4-t-butylphenyl)phosphate, and tris(4-cyclohexylphenyl)phosphate; and compounds obtained by partly fluorinating these aromatic compounds, such as 2-fluorobiphenyl, 3-fluorobiphenyl, 4-fluorobiphenyl, 4,4'-difluorobiphenyl, o-cyclohexylfluorobenzene, and p-cyclohexylfluorobenzene.

More preferred of these are partly hydrogenated terphenyls, cyclopentylbenzene, cyclohexylbenzene, cis-1-propyl-4-phenylcyclohexane, trans-1-propyl-4-phenylcyclohexane, cis-1-butyl-4-phenylcyclohexane, trans-1-butyl-4-phenylcyclohexane, t-butylbenzene, t-amylbenzene, methyl phenyl carbonate, diphenyl carbonate, methyl phenyl sulfonate, diphenyl sulfonate, triphenyl phosphate, tris(4-t-butylphenyl)phosphate, tris(4-cyclohexylphenyl)phosphate, o-cyclohexylfluorobenzene, and p-cyclohexylfluorobenzene. Especially preferred are partly hydrogenated terphenyls and cyclohexylbenzene.

Two or more of these compounds may be used in combination. In the case of using two or more compounds in combination, it is especially preferred to use a combination of a partly hydrogenated terphenyl or cyclohexylbenzene with t-butylbenzene or t-amylbenzene or to use a compound selected from aromatic compounds containing no oxygen, such as biphenyl, alkylbiphenyls, terphenyl, partly hydrogenated terphenyls, cyclohexylbenzene, t-butylbenzene, and t-amylbenzene, in combination with a compound selected from oxygen-containing aromatic compounds such as diphenyl ether and dibenzofuran, from the standpoint of a balance between overcharge preventive properties and high-temperature storability.

The proportion of these overcharge inhibitors in the nonaqueous electrolytic solution is preferably 0.1% by mass or higher, more preferably 0.2% by mass or higher, even more preferably 0.3% by mass or higher, especially preferably 0.5% by mass or higher, and is preferably 5% by mass or less, more preferably 3% by mass or less, even more preferably 2% by mass or less. In cases when the proportion thereof is within that range, the desired effect of the overcharge inhibitors is sufficiently exhibited and battery characteristics including high-temperature storability are prevented from decreasing.

Other examples of the aids include: carbonate compounds such as erythritan carbonate, spirobisdimethylene carbonate, methoxyethyl methyl carbonate, methoxyethyl ethyl carbonate, ethoxyethyl methyl carbonate, and ethoxyethyl ethyl carbonate; carboxylic acid anhydrides such as succinic anhydride, glutaric anhydride, maleic anhydride, itaconic anhydride, citraconic anhydride, glutaconic anhydride, diglycolic anhydride, cyclohexanedicarboxylic anhydride, cyclopentanetetracarboxylic dianhydride, and phenylsuccinic anhydride; dicarboxylic acid diester compounds such as dimethyl succinate, diethyl succinate, diallyl succinate, dimethyl maleate, diethyl maleate, diallyl maleate, dipropyl maleate, dibutyl maleate, bis(trifluoromethyl) maleate, bis(pentafluoroethyl) maleate, and bis(2,2,2-trifluoroethyl) maleate; spiro compounds such as 2,4,8,10-tetraoxaspiro[5.5]undecane and 3,9-divinyl-2,4,8,10-tetraoxaspiro[5.5]undecane; sulfur-containing compounds such as ethylene sulfite, propylene sulfite, 1,3-propanesultone, 1,4-butanesultone, 1,3-propenesultone, 1,4-butenesultone, methyl methanesulfonate, ethyl methanesulfonate, methyl methoxymethanesulfonate, methyl 2-methoxyethanesulfonate, busulfan, diethylene glycol dimethanesulfonate, 1,2-ethanediol bis(2,2,2-trifluoroethanesulfonate), 1,4-butanediol bis(2,2,2-trifluoroethanesulfonate), sulfolane, 3-sulfolene, 2-sulfolene, dimethyl sulfone, diethyl sulfone, divinyl sulfone, diphenyl sulfone, bis(methylsulfonyl)methane, bis(methylsulfonyl)ethane, bis(ethylsulfonyl)methane, bis(ethylsulfonyl)ethane, bis(vinylsulfonyl)methane, bis(vinylsulfonyl)ethane, N,N-dimethylmethanesulfonamide, N,N-diethylmethanesulfonamide, N,N-dimethyltrifluoromethanesulfonamide, and N,N-diethyltrifluoromethanesulfonamide; nitrogen-containing compounds such as 1-methyl-2-pyrrolidinone, 1-methyl-2-piperidone, 3-methyl-2-oxazolidinone, 1,3-dimethyl-2-imidazolidinone, and N-methylsuccinimide; hydrocarbon compounds such as heptane, octane, nonane, decane, cycloheptane, methylcyclohexane, ethylcyclohexane, propylcyclohexane, n-butylcyclohexane, t-butylcyclohexane, and dicyclohexyl; fluorinated benzenes such as fluorobenzene, difluorobenzene, pentafluorobenzene, and hexafluorobenzene; fluorinated toluenes such as 2-fluorotoluene, 3-fluorotoluene, 4-fluorotoluene, and benzotrifluoride; nitrile compounds such as acetonitrile, propionitrile, butyronitrile, malononitrile, succinonitrile, glutaronitrile, adiponitrile, and pimelonitrile; and phosphorus-containing compounds such as methyl dimethylphosphinate, ethyl dimethylphosphinate, ethyl diethylphosphinate, trimethyl phosphonoformate, triethyl phosphonoformate, trimethyl phosphonoacetate, triethyl phosphonoacetate, trimethyl 3-phosphonopropionate, and triethyl 3-phosphonopropionate.

Preferred of these, from the standpoint of improving the characteristics of the battery which has undergone high-temperature storage, are sulfur-containing compounds such as ethylene sulfite, 1,3-propanesultone, 1,4-butanesultone, 1,3-propenesultone, 1,4-butenesultone, busulfan, and 1,4-butanediol bis(2,2,2-trifluoroethanesulfonate) and nitrile compounds such as acetonitrile, propionitrile, butyronitrile, malononitrile, succinonitrile, glutaronitrile, adiponitrile, and pimelonitrile.

Two or more of these compounds may be used in combination. There are no particular limitations on the proportion of these aids in the nonaqueous electrolytic solution. However, the proportion thereof is preferably 0.01% by mass or higher, more preferably 0.1% by mass or higher, even more preferably 0.2% by mass or higher, and is preferably 8% by mass or less, more preferably 5% by mass or less, even more preferably 3% by mass or less, especially preferably 1% by mass or less.

Addition of these aids is preferred from the standpoint of improving capacity retentivity after high-temperature storage and cycling characteristics. In cases when the proportion thereof is within that range, the effects of the aids are sufficiently produced and battery characteristics including high-load discharge characteristics are prevented from decreasing.

(Preparation of the Electrolytic Solution)

The nonaqueous electrolytic solution according to the invention can be prepared by dissolving an electrolyte and a compound represented by general formula (I) and/or compound represented by general formula (II) in a nonaqueous solvent optionally together with other compounds.

It is preferable that prior to the preparation of the nonaqueous electrolytic solution, these ingredients should be dehydrated beforehand in order that the electrolytic solution to be obtained have a reduced water content. It is desirable that each ingredient be dehydrated to a water content of preferably 50 ppm or less, more preferably 30 ppm or less, even more preferably 10 ppm or less. Use may also be made of a method in which an electrolytic solution is prepared and is thereafter subjected to dehydration, deacidifying treatment, etc.

The nonaqueous electrolytic solution of the invention is suitable for use as a nonaqueous electrolytic solution for nonaqueous-electrolyte batteries, in particular, secondary batteries, i.e., nonaqueous-electrolyte secondary batteries, e.g., lithium secondary batteries. A nonaqueous-electrolyte secondary battery employing the nonaqueous electrolytic solution of the invention is explained below.

<Nonaqueous-Electrolyte Secondary Battery>

The nonaqueous-electrolyte secondary battery of the invention is a nonaqueous-electrolyte battery which includes a negative electrode and a positive electrode that are capable of occluding and releasing lithium ions and a nonaqueous electrolytic solution, and which is characterized in that the nonaqueous electrolytic solution is the nonaqueous electrolytic solution according to the invention.

(Battery Configuration)

The nonaqueous-electrolyte secondary battery according to the invention is a nonaqueous-electrolyte battery which includes a negative electrode and a positive electrode that are capable of occluding and releasing lithium ions and a nonaqueous electrolytic solution like conventionally known nonaqueous-electrolyte secondary batteries, except that this battery is produced using the nonaqueous electrolytic solution according to the invention. Usually, the battery of the invention is obtained by disposing a positive electrode and a negative electrode in a case, with a porous film interposed therebetween, the porous film having been impregnated with the nonaqueous electrolytic solution of the invention.

Consequently, the shape of the nonaqueous-electrolyte secondary battery of the invention is not particularly limited, and may be any of cylindrical, prismatic, laminate type, coin type, large-size, and other shapes.

(Negative-Electrode Active Material)

Usable negative-electrode active materials are not particularly limited so long as the active materials are capable of occluding and releasing lithium ions. Examples thereof include carbonaceous materials, alloy-based materials, and lithium-containing metal composite oxide materials.

These negative-electrode active materials may be used either alone or as a mixture of two or more thereof. Preferred of these are carbonaceous materials and alloy-based materials.

Preferred of the carbonaceous materials are amorphous carbon materials, graphites, and materials obtained by coating the surface of a graphite with carbon which is more amorphous than the graphite. Especially preferred are graphites and materials obtained by coating the surface of a graphite with carbon which is more amorphous than the graphite. This is because such active materials generally have a high energy density.

Preferred graphites are ones in which the value of d (interplanar spacing) of the lattice planes (002), as determined by X-ray diffractometry by the method of the Japan Society for Promotion of Scientific Research, is 0.335-0.338 nm, in particular, 0.335-0.337 nm.

The crystallite size (Lc) thereof determined by X-ray diffractometry by the method of the Japan Society for Promotion of Scientific Research is preferably 10 nm or larger, more preferably 50 nm or larger, even more preferably 100 nm or larger.

The ash content thereof is preferably 1% by mass or less, more preferably 0.5% by mass or less, even more preferably 0.1% by mass or less.

Preferred of the materials obtained by coating the surface of a graphite with amorphous carbon is one that is configured of a graphite, as a core material, in which the value of d of the lattice planes (002) determined by X-ray diffractometry is 0.335-0.338 nm and a carbonaceous material adherent to the surface of the core material, the carbonaceous material having a larger value of lattice-plane (002) d by X-ray diffractometry than the core material, the proportion of the core material to the carbonaceous material, which has a larger value of lattice-plane (002) d by X-ray diffractometry than the core material, being 99/1 to 80/20 in terms of mass ratio. Use of this active material enables a high capacity to be obtained and makes it possible to produce a negative electrode which is less apt to react with the electrolytic solution.

The particle diameter of the carbonaceous material, in terms of median diameter determined by the laser diffraction/scattering method, is preferably 1 μm or larger, more preferably 3 μm or larger, even more preferably 5 μm or larger, especially preferably 7 μm or larger, and is preferably 100 μm or less, more preferably 50 μm or less, even more preferably 40 μm or less, especially preferably 30 μm or less.

The specific surface area of the carbonaceous material, as determined by the BET method, is preferably 0.3 m$^2$/g or larger, more preferably 0.5 m$^2$/g or larger, even more preferably 0.7 m$^2$/g or larger, especially preferably 0.8 m$^2$/g or larger, and is preferably 25.0 m$^2$/g or less, more preferably 20.0 m$^2$/g or less, even more preferably 15.0 m$^2$/g or less, especially preferably 10.0 m$^2$/g or less.

Furthermore, it is preferable that the carbonaceous material should be one which, when analyzed by Raman spectroscopy using argon ion laser light, has a value of R represented by the ratio of $I_B$ to $I_A$ (i.e., $I_B/I_A$) in the range of 0.01-0.7, wherein $I_A$ is the peak intensity at the peak $P_A$ present in the range of 1,570-1,620 cm$^{-1}$ and $I_B$ is the peak intensity at the peak $P_B$ present in the range of 1,300-1,400 cm$^{-1}$.

Also preferred is a carbonaceous material in which the peak present in the range of 1,570-1,620 cm$^{-1}$ has a half-value width of 26 cm$^{-1}$ or less, in particular, 25 cm$^{-1}$ or less.

The alloy-based materials are not particularly limited so long as the materials are capable of occluding and releasing lithium. Use may be made of any of elemental metals and alloys which form lithium alloys or compounds of these metals, such as oxides, carbides, nitrides, silicides, sulfides, and phosphides. Preferred are materials which include an elemental metal and alloy that form a lithium alloy. More preferred are materials which include any of the metallic and metalloid elements in Group 13 and Group 14 (i.e., carbon is excluded). Even more preferred are the elemental metals of aluminum, silicon, and tin (these elements are hereinafter often referred to as "specific metallic elements") and alloys or compounds containing these elements.

Example of the negative-electrode active material which includes at least one element selected from the specific metallic elements include the elemental metal of any one of the specific metallic elements, an alloy constituted of two or more of the specific metallic elements, an alloy constituted of one or more of the specific metallic elements with one or more other metallic elements, a compound which contains one or more of the specific metallic elements, and a composite compound of that compound, such as an oxide, carbide, nitride, silicide, sulfide, or phosphide.

Use of any of such metallic elements, alloys, or metal compounds as a negative-electrode active material renders an increase in battery capacity possible.

Examples thereof further include compounds in which those composite compounds have complicatedly combined with an elemental metal, an alloy, or a plurality of elements, e.g., nonmetallic elements. More specifically, in the case of silicon and tin, for example, use can be made of alloys of these elements with a metal which does not work as a negative electrode. Furthermore, tin, for example, can be used in the form of a complicated compound including 5-6 elements which are a combination of tin, one or more metals that are not silicon and function as a negative electrode, one or more metals that do not work as a negative electrode, and one or more nonmetallic elements.

Preferred of these negative-electrode active materials are the elemental metal of any one of the specific metallic elements, alloys of two or more of the specific metallic elements, and oxides, carbides, nitrides, and the like of specific metallic elements. This is because these active materials have a high capacity per unit mass in batteries. In particular, the elemental metal(s), alloys, and oxides, carbides, nitrides, and the like of silicon and/or tin are preferred because these active materials have a high capacity per unit mass.

The following compounds which contain silicon and/or tin are also preferred because the following compounds are excellent in terms of cycling characteristics although inferior in capacity per unit mass to the elemental metals or alloys.

An oxide of silicon and/or tin in which the element ratio of silicon and/or tin to oxygen is preferably 0.5 or larger, more preferably 0.7 or larger, even more preferably 0.9 or larger, and is preferably 1.5 or less, more preferably 1.3 or less, even more preferably 1.1 or less.

A nitride of silicon and/or tin in which the element ratio of silicon and/or tin to nitrogen is preferably 0.5 or larger, more preferably 0.7 or larger, even more preferably 0.9 or larger, and is preferably 1.5 or less, more preferably 1.3 or less, even more preferably 1.1 or less.

A carbide of silicon and/or tin in which the element ratio of silicon and/or tin to carbon is preferably 0.5 or larger, more preferably 0.7 or larger, even more preferably 0.9 or larger, and is preferably 1.5 or less, more preferably 1.3 or less, even more preferably 1.1 or less.

These alloy-based materials may be in a powder form or thin-film form, and may be crystalline or amorphous.

The average particle diameter of such an alloy-based material is not particularly limited from the standpoint of producing the effects of the invention. However, the average particle diameter thereof is preferably 50 μm or less, more preferably 20 μm or less, even more preferably 10 μm or less, and is preferably 0.1 μm or larger, more preferably 1 μm or larger, even more preferably 2 μm or larger.

In case where the particle diameter thereof is too large, there is a possibility that the electrode might show enhanced expansion, resulting in a decrease in cycling characteristics. Meanwhile, in case where the particle diameter thereof is too small, there is a possibility that current collection might be difficult and the capacity might not be sufficiently exhibited.

The lithium-containing metal composite oxide materials usable as negative-electrode active materials are not particularly limited so long as the composite oxide materials are capable of occluding and releasing lithium. However, composite oxides of lithium and titanium (hereinafter abbreviated to "lithium-titanium composite oxides") are preferred.

Also preferred are lithium-titanium composite oxides in which the lithium and the titanium have been partly replaced with other metallic element(s), e.g., at least one element selected from the group consisting of Na, K, Co, Al, Fe, Mg, Cr, Ga, Cu, Zn, and Nb.

Furthermore, lithium-titanium composite oxides represented by $Li_xTi_yM_zO_4$ in which $0.7 \le x \le 1.5$, $1.5 \le y \le 2.3$, and $0 \le z \le 1.6$ are preferred because these composite oxides retain a stable structure when lithium ions are occluded and released (M represents at least one element selected from the group consisting of Na, K, Co, Al, Fe, Mg, Cr, Ga, Cu, Zn, and Nb).

Preferred of these are lithium-titanium composite oxides represented by $Li_xTi_yM_zO_4$ in which $z=0$ and x and y satisfy any of the following (a) to (c), because this structure brings about a satisfactory balance among battery performances.

(a) $1.2 \le x \le 1.4$, $1.5 \le y \le 1.7$, $z=0$
(b) $0.9 \le x \le 1.1$, $1.9 \le y \le 2.1$, $z=0$
(c) $0.7 \le x \le 0.9$, $2.1 \le y \le 2.3$, $z=0$

More preferred representative compositions are $Li_{4/3}Ti_{5/3}O_4$ for (a), $Li_1Ti_2O_4$ for (b), and $Li_{4/5}Ti_{11/5}O_4$ for (c).

Meanwhile, with respect to the structures in which $z \ne 0$, preferred examples thereof include $Li_{4/3}Ti_{4/3}Al_{1/3}O_4$.

(Positive-Electrode Active Material)

Usable positive-electrode active materials are not particularly limited so long as the active materials are capable of occluding and releasing lithium ions. A material which includes lithium and at least one transition metal is preferred, and examples thereof include lithium-transition metal composite oxides and lithium-containing transition metal phosphoric-acid compounds.

The transition metals of the lithium-transition metal composite oxides preferably are V, Ti, Cr, Mn, Fe, Co, Ni, Cu, etc. Examples of the composite oxides include lithium-cobalt composite oxides such as $LiCoO_2$, lithium-nickel composite oxides such as $LiNiO_2$, and lithium-manganese composite oxides such as $LiMnO_2$, $LiMn_2O_4$, and $Li_2MnO_3$.

Also usable are those lithium-transition metal composite oxides in which the transition metal atoms as main components thereof have been partly replaced with other metal(s). Examples thereof include: lithium-cobalt composite oxides in which the Co has been partly replaced with other metal(s) such as Al, Ti, V, Cr, Mn, Fe, Li, Ni, Cu, Zn, Mg, Ga, Zr, Si, etc.; lithium-nickel composite oxides in which the Ni has been partly replaced with other metal(s) such as Al, Ti, V, Cr, Mn, Fe, Co, Li, Cu, Zn, Mg, Ga, Zr, Si, etc.; and lithium-manganese composite oxides in which the Mn has been partly replaced with other metal(s) such as Al, Ti, V, Cr, Fe, Co, Li, Ni, Cu, Zn, Mg, Ga, Zr, Si, etc.

Preferred of such lithium-transition metal composite oxides in which the transition metal atoms as main components thereof have been partly replaced with other metal(s) are: $LiNi_{1-a-b}Mn_aCo_bO_2$ (a and b each independently represent a number of 0 or larger but less than 1, with the proviso that the case where a and b are both 0 is excluded); and $LiNi_{1-c-d-e}Co_cAl_dMg_eO_2$ (c, d, and e each independently represent a number of 0 or larger but less than 1, with the proviso that the case where all of c, d, and e are 0 is excluded).

More preferred are $LiNi_{1-a-b}Mn_aCo_bO_2$ ($0 \le a < 0.4$, $0 \le b < 0.4$) and $LiNi_{1-c-d-e}Co_cAl_dMg_eO_2$ ($0 \le c < 0.3$, $0 \le d < 0.1$, $0 \le e < 0.05$). Especially preferred are $LiNi_{1/3}Co_{1/3}Mn_{1/3}O_2$, $LiNi_{0.5}Co_{0.3}Mn_{0.2}O_2$, $LiNi_{0.5}Mn_{0.5}O_2$, $LiNi_{0.85}Co_{0.10}Al_{0.05}O_2$, and $LiNi_{0.85}Co_{0.10}Al_{0.03}Mg_{0.02}O_2$.

The transition metals of the lithium-containing transition metal phosphoric-acid compounds preferably are V, Ti, Cr, Mn, Fe, Co, Ni, Cu, etc. Examples of the phosphoric-acid compounds include iron phosphate compounds such as $LiFePO_4$, $Li_3F_2(PO_4)_3$, and $LiFeP_2O_7$ and cobalt phosphate compounds such as $LiCoPO_4$.

Examples thereof further include those lithium-containing transition metal phosphoric-acid compounds in which the transition metal atoms as main components thereof have been partly replaced with other metal(s), such as the iron phosphate compounds in which the Fe has been partly replaced with other metal(s) such as Al, Ti, V, Cr, Mn, Co, Li, Ni, Cu, Zn, Mg, Ga, Zr, Nb, Si, etc. and the cobalt phosphate compounds in which the Co has been partly replaced with other metal(s) such as Al, Ti, V, Cr, Mn, Fe, Li, Ni, Cu, Zn, Mg, Ga, Zr, Nb, Si, etc.

These positive-electrode active materials may be used either alone or in combination of two or more thereof.

It is also possible to use a material which includes any of those positive-electrode active materials and a substance (surface-adherent substance) adherent to the surface thereof and having a composition different from that of the substance constituting the positive-electrode active material as the main component.

Examples of the surface-adherent substance include: oxides such as aluminum oxide, silicon oxide, titanium oxide, zirconium oxide, magnesium oxide, calcium oxide, boron oxide, antimony oxide, and bismuth oxide; sulfates such as lithium sulfate, sodium sulfate, potassium sulfate, magnesium sulfate, calcium sulfate, and aluminum sulfate; and carbonates such as lithium carbonate, calcium carbonate, and magnesium carbonate.

The amount of the surface-adherent substance is not particularly limited from the standpoint of producing the effects of the invention. However, the surface-adherent substance may be used in an amount which is preferably 0.1 ppm or larger, more preferably 1 ppm or larger, even more preferably 10 ppm or larger, and is preferably 20% or less, more preferably 10% or less, even more preferably 5% or less, in terms of mass amount based on the positive-electrode active material.

By the action of the surface-adherent substance, the nonaqueous electrolytic solution can be inhibited from undergoing oxidation reaction on the surface of the positive-electrode active material and the battery life can be improved. However, in case where the adhesion amount thereof is too small, the effects thereof are not sufficiently produced. Too large adhesion amounts thereof may result in cases where the surface-adherent substance inhibits lithium ions from going in and out, resulting in an increase in resistance.

(Production of Electrodes)

Any desired binders for binding the active materials can be used so long as the binders are materials which are stable to the solvent to be used in electrode production and to the electrolytic solution.

Examples thereof include: fluororesins such as poly(vinylidene fluoride) and polytetrafluoroethylene; polyolefins such as polyethylene and polypropylene; polymers having unsaturated bonds, such as styrene/butadiene rubbers, isoprene rubber, and butadiene rubber; and acrylic acid polymers such as ethylene/acrylic acid copolymers and ethylene/methacrylic acid copolymers.

A thickener, conductive material, filler, etc. may be incorporated into the electrodes in order to enhance the mechanical strength and the electrical conductivity.

Examples of the thickener include carboxymethyl cellulose, methyl cellulose, hydroxymethyl cellulose, ethyl cellulose, poly(vinyl alcohol), oxidized starch, phosphorylated starch, and casein.

Examples of the conductive material include metallic materials such as copper or nickel and carbon materials such as a graphite or carbon black.

The electrodes may be produced by ordinary methods. For example, the negative electrode or the positive electrode can be formed by adding a binder, thickener, conductive material, solvent, etc. to a negative-electrode or positive-electrode active material to obtain a slurry, applying the slurry to a current collector, drying the slurry applied, and then pressing the coated current collector.

Alternatively, use can be made of: a method in which a mixture prepared by adding a binder, conductive material, etc. to an active material is subjected as such to roll forming to produce a sheet electrode or to compression molding to produce a pellet electrode; or a method in which a thin film of an electrode material is formed on a current collector by a technique such as vapor deposition, sputtering, or plating.

In the case where a graphite has been used as the negative-electrode active material, the density of the negative-electrode active-material layer which has undergone drying and pressing is preferably 1.45 g/cm$^3$ or higher, more preferably 1.55 g/cm$^3$ or higher, even more preferably 1.60 g/cm$^3$ or higher, especially preferably 1.65 g/cm$^3$ or higher.

The density of the positive-electrode active-material layer which has undergone drying and pressing is preferably 2.0 g/cm$^3$ or higher, more preferably 2.5 g/cm$^3$ or higher, even more preferably 3.0 g/cm$^3$ or higher.

As the current collectors, various known current collectors can be used. Usually, however, metals or alloys are used. Examples of the current collector of the negative electrode include copper, nickel, and stainless steel, and copper is preferred. Examples of the current collector of the positive electrode include metals such as aluminum, titanium, and tantalum or alloys thereof. Preferred of these is aluminum or alloys thereof.

(Separator and Case)

A porous membrane (separator) is interposed between the positive electrode and the negative electrode in order to prevent short-circuiting. In this case, the electrolytic solution is infiltrated into the porous membrane and used. There are no particular limitations on the material and shape of the porous membrane, so long as the porous membrane is stable to the electrolytic solution and has excellent liquid retentivity. Preferred is a porous sheet, nonwoven fabric, or the like formed from a polyolefin, e.g., polyethylene or polypropylene.

The material of the battery case to be used in the battery according to the invention is also not limited. Use can be made of nickel-plated iron, stainless steel, aluminum or an alloy thereof, nickel, titanium, a laminated film, etc.

The nonaqueous-electrolyte secondary battery of the invention described above has an operating voltage usually in the range of 2-4.9 V.

EXAMPLES

The invention will be explained below in more detail by reference to Examples and Comparative Examples. However, the invention should not be construed as being limited to the following Examples unless the invention departs from the spirit thereof.

The batteries obtained in the following Examples and Comparative Examples were evaluated by the methods shown below.

[Capacity Evaluation]

Each sheet-form nonaqueous-electrolyte secondary battery was evaluated in the state of being sandwiched between glass plates in order to enhance contact between the electrodes. At 25° C., this battery was charged to 4.1 V at a constant current corresponding to 0.3 C and then discharged to 3 V at a constant current of 0.3 C. Five cycles of this charge/discharge were conducted to stabilize the battery. In the fourth cycle, the battery was charged to 4.1 V at a constant current of 0.3 C, subsequently charged at a constant voltage of 4.1 V until the current value became 0.05 C, and then discharged to 3 V at a constant current of 0.3 C to determine initial discharge capacity.

Here, "1 C" means a current value at which the reference capacity of the battery is discharged over 1 hour. For example, "0.3 C" means the current value which is 0.3 times the current of 1 C.

Incidentally, when the state of charge (SOC) of a battery is expressed, the SOC of the battery having a voltage of 3 V is regarded as 0% and that of the battery having a voltage of 4.1 V is regarded as 100%. Using the initial discharge capacity as a reference for 100%, the SOC (%) of the battery can be calculated from a quantity charged. For example, in the case where a battery of 4.1 V (SOC, 100%) is charged in the same quantity as the initial capacity, the state of charge of this battery is expressed as SOC 200%.

[Output Evaluation]

With respect to Examples B-1 to B-6, Comparative Examples B-1 to B-5, and Reference Example B-1, the batteries produced in the manners described above were charged at room temperature and at a constant current of 0.3 C from 3 V to one-half the reference capacity of the battery (50% of full charge), subsequently allowed to stand in a −30° C. thermostatic chamber for 2 hours or longer, and then examined for output.

[Evaluation of Overcharge Characteristics]

With respect to Examples A-1 and A-2 and Comparative Examples A-1 to A-10, the batteries which had undergone the capacity evaluation test were evaluated in the following manner. At 25° C., each battery was charged to 4.1 V at a constant current of 0.3 C, subsequently charged at a constant voltage of 4.1 V until the current value became 0.05 C, and then immersed in an ethanol bath to measure the volume thereof. Thereafter, at 45° C., a constant current of 1.0 C was applied to the battery and the current was cut off at the time when the voltage had reached 4.9 V. The open-circuit voltage (OCV) of this battery which had undergone the overcharge test was measured.

With respect to Examples B-1 to B-6, Comparative Examples B-1 to B-5, and Reference Example B-1, the batteries which had undergone the output evaluation test were evaluated in the following manner. At 25° C., each battery was charged to 4.1 V at a constant current of 0.3 C, subsequently charged at a constant voltage of 4.1 V until the current value became 0.05 C, and then immersed in an ethanol bath to measure the volume thereof. Thereafter, at 45° C., a constant current of 0.5 C was applied to the battery and the current was cut off at the time when an SOC of 180% had been reached. The open-circuit voltage (OCV) of this battery which had undergone the overcharge test was measured.

Each battery which had undergone the OCV measurement was immersed in an ethanol bath to measure the volume thereof. The amount of the gas which had been evolved was determined from the difference in volume between before and after the overcharge.

The lower the OCV of a battery which has undergo the overcharge test, the lower the state of overcharge thereof and the higher the safety thereof during overcharge. Furthermore, the larger the amount of evolved gas after the overcharge, the more the battery is preferred in the case where this battery is of the type in which an abnormal increase in internal pressure due to an abnormality, e.g., overcharge, is sensed to make the safety value work. This is because the safety valve can operate in an early stage.

Moreover, it is preferable that the difference between the amount of evolved gas after the overcharge and the amount of gas which is evolved during high-temperature storage or the like should be larger, because it is possible to prevent the safety valve from erroneously working during high-temperature storage or the like, while making the safety valve work in overcharge without fail.

[Evaluation of High-Temperature Storability]

At 25° C., each battery which had undergone the capacity evaluation test or the output evaluation test was charged to 4.1 V at a constant current of 0.3 C, subsequently charged at a constant voltage of 4.1 V until the current value became 0.05 C, and then immersed in an ethanol bath to measure the volume thereof. Thereafter, a high-temperature storage test was conducted at 75° C. for 72 hours (3 days).

After the high-temperature storage test, the battery was cooled to 25° C. and then immersed in an ethanol bath to measure the volume thereof. The amount of the gas which had been evolved was determined from the difference in volume between before and after the high-temperature storage.

After the determination of the amount of evolved gas, the battery was discharged to 3 V at a constant current of 0.3 C at 25° C. to measure the residual capacity remaining after the high-temperature storage test.

Next, at 25° C., the battery was charged to 4.1 V at a constant current of 0.3 C, subsequently charged at a constant voltage of 4.1 V until the current value became 0.05 C, and then discharged to 3 V at a constant current of 0.3 C to measure the 0.3 C discharge capacity of the battery which had undergone the high-temperature storage test.

Furthermore, with respect to Examples B-1 to B-6, Comparative Examples B-1 to B-5, and Reference Example B-1, the batteries charged to an SOC of 50% were examined for output in a −30° C. thermostatic chamber.

Example A-1

[Production of Positive Electrode]

In N-methylpyrrolidone solvent, 90% by mass lithium-cobalt-nickel-manganese oxide ($LiNi_{1/3}Co_{1/3}Mn_{1/3}O_2$) as a positive-electrode active material was mixed with 7% by mass acetylene black as a conductive material and 3% by mass poly(vinylidene fluoride) (PVdF) as a binder by means of a disperser. Thus, a slurry was obtained. This slurry was evenly applied to both surfaces of an aluminum foil and dried, and the resultant coated foil was pressed to obtain a positive electrode.

[Production of Negative Electrode]

Ninety-eight parts by mass of a graphite powder as a negative-electrode active material was mixed with 2 parts by mass of PVdF, and N-methylpyrrolidone was added thereto to obtain a slurry. This slurry was applied to one surface of a current collector made of copper, and the slurry applied was dried to obtain a negative electrode.

[Production of Electrolytic Solution]

In a dry argon atmosphere, a mixture of ethylene carbonate, ethyl methyl carbonate, and dimethyl carbonate (volume ratio, 3:4:3) was mixed with 2% by mass methyl 3-phenylpropyl carbonate, in terms of content in the nonaqueous electrolytic solution, as shown in Table 1. Subsequently, sufficiently dried $LiPF_6$ was dissolved therein so as to result in a proportion thereof of 1.0 mol/L. Thus, an electrolytic solution was obtained.

[Production of Nonaqueous-Electrolyte Secondary Battery]

The positive electrode and negative electrode described above and a separator made of polyethylene were stacked in the order of negative electrode/separator/positive electrode/separator/negative electrode to produce a battery element. This battery element was inserted into a bag constituted of a laminated film obtained by coating both surfaces of aluminum (thickness, 40 μm) with a resin layer, with the terminals of the positive and negative electrodes projecting outward. Thereafter, the electrolytic solution was injected into the bag, and this bag was vacuum-sealed to produce a sheet-form battery. This battery was evaluated for overcharge characteristics and high-temperature storability. The results of the evaluation are shown in Table 1.

Example A-2

A sheet-form battery was produced and evaluated for overcharge characteristics and high-temperature storability in the same manners as in Example A-1, except that 0.5% by mass vinylene carbonate was further added in preparing the electrolytic solution of Example A-1. The results of the evaluation are shown in Table 1.

Comparative Example A-1

A sheet-form battery was produced and evaluated for overcharge characteristics and high-temperature storability in the same manners as in Example A-1, except that the methyl 3-phenylpropyl carbonate was omitted in preparing the electrolytic solution of Example A-1. The results of the evaluation are shown in Table 1.

Comparative Example A-2

A sheet-form battery was produced and evaluated for overcharge characteristics and high-temperature storability in the same manners as in Example A-1, except that cyclohexylbenzene was used in place of the methyl 3-phenylpropyl carbonate in preparing the electrolytic solution of Example A-1. The results of the evaluation are shown in Table 1.

Comparative Example A-3

A sheet-form battery was produced and evaluated for overcharge characteristics and high-temperature storability in the same manners as in Example A-1, except that methyl phenyl carbonate was used in place of the methyl 3-phenylpropyl carbonate in preparing the electrolytic solution of Example A-1. The results of the evaluation are shown in Table 1.

Comparative Example A-4

A sheet-form battery was produced and evaluated for overcharge characteristics and high-temperature storability in the same manners as in Example A-1, except that n-butylbenzene was used in place of the methyl 3-phenylpropyl carbonate in preparing the electrolytic solution of Example A-1. The results of the evaluation are shown in Table 1.

Comparative Example A-5

A sheet-form battery was produced and evaluated for overcharge characteristics and high-temperature storability in the same manners as in Example A-1, except that 3-phenylpropyl acetate was used in place of the methyl 3-phenylpropyl carbonate in preparing the electrolytic solution of Example A-1. The results of the evaluation are shown in Table 1.

Comparative Example A-6

A sheet-form battery was produced and evaluated for overcharge characteristics and high-temperature storability in the same manners as in Example A-1, except that phenethyl butyrate was used in place of the methyl 3-phenylpropyl carbonate in preparing the electrolytic solution of Example A-1. The results of the evaluation are shown in Table 1.

Comparative Example A-7

A sheet-form battery was produced and evaluated for overcharge characteristics and high-temperature storability in the same manners as in Example A-1, except that 0.5% by mass vinylene carbonate was used in place of the methyl 3-phenylpropyl carbonate in preparing the electrolytic solution of Example A-1. The results of the evaluation are shown in Table 1.

Comparative Example A-8

A sheet-form battery was produced and evaluated for overcharge characteristics and high-temperature storability in the same manners as in Example A-1, except that 2% by mass cyclohexylbenzene and 0.5% by mass vinylene carbonate were used in place of the methyl 3-phenylpropyl carbonate in preparing the electrolytic solution of Example A-1. The results of the evaluation are shown in Table 1.

Comparative Example A-9

A sheet-form battery was produced and evaluated for overcharge characteristics and high-temperature storability in the same manners as in Example A-1, except that benzyl methyl carbonate was used in place of the methyl 3-phenylpropyl carbonate in preparing the electrolytic solution of Example A-1. The results of the evaluation are shown in Table 1.

Comparative Example A-10

A sheet-form battery was produced and evaluated for overcharge characteristics and high-temperature storability in the same manners as in Example A-1, except that 2% by mass benzyl methyl carbonate and 0.5% by mass vinylene carbonate were used in place of the methyl 3-phenylpropyl carbonate in preparing the electrolytic solution of Example A-1. The results of the evaluation are shown in Table 1.

Example B-1

[Production of Electrolytic Solution]

In a dry argon atmosphere, vinylene carbonate was added to a mixture of ethylene carbonate, ethyl methyl carbonate, and dimethyl carbonate (volume ratio, 3:4:3) in an amount of 0.5% by mass in terms of content in the nonaqueous electrolytic solution. Furthermore, 2,2-bis(p-methoxycarbonyloxyphenyl)propane was added in such an amount as to result in a content thereof of 2.2% by mass. Subsequently, sufficiently dried $LiPF_6$ was dissolved therein so as to result in a proportion thereof of 1.0 mol/L. Thus, an electrolytic solution was obtained. For the evaluation of overcharge characteristics, however, a nonaqueous electrolytic solution prepared without adding vinylene carbonate was used. Incidentally, it is thought that whether vinylene carbonate is present or absent does not considerably affect the overcharge characteristics.

A sheet-form battery was produced in the same manner as in Example A-1, except for the production of the electrolytic solution. This battery was evaluated for overcharge characteristics, output characteristics, and high-temperature storability. The results of the evaluation are shown in Table 2.

Incidentally, the 2,2-bis(p-methoxycarbonyloxyphenyl) propane used was a synthesized product of Mitsubishi Chemical Corp.

Example B-2

A sheet-form battery was produced and evaluated for overcharge characteristics, output characteristics, and high-temperature storability in the same manners as in Example B-1, except that 2,2-bis(p-methoxycarbonyloxyphenyl)propane was added in an amount of 1.1% by mass in preparing the electrolytic solution of Example B-1. The results of the evaluation are shown in Table 2.

Example B-3

A sheet-form battery was produced and evaluated for overcharge characteristics, output characteristics, and high-temperature storability in the same manners as in Example B-1, except that 1,1-bis(p-methoxycarbonyloxyphenyl)cyclohexane was added in an amount of 2.4% by mass in place of the 2,2-bis(p-methoxycarbonyloxyphenyl)propane in preparing the electrolytic solution of Example B-1. The results of the evaluation are shown in Table 2.

Incidentally, the 1,1-bis(p-methoxycarbonyloxyphenyl)cyclohexane was synthesized by the following method.

A dropping funnel was attached to a 2.0-L four-necked flask, and the atmosphere therein was replaced with a nitrogen atmosphere. Thereinto was introduced 100.0 g (372 mmol) of bisphenol A, followed by dichloromethane (400 mL) and triethylamine (190 mL; 1,363 mmol). The resultant mixture was stirred. While the mixture was being cooled with ice, 121.3 g (1,284 mmol) of methyl chloroformate was added dropwise thereto and this mixture was stirred for 30 minutes. Thereafter, water was added to terminate the reaction.

The resultant liquid reaction mixture was extracted with dichloromethane three times, and the organic layers were mixed together. The mixed organic layer was washed successively with dilute hydrochloric acid, water, and an aqueous sodium chloride solution and dried with anhydrous sodium sulfate. The solvent was distilled off, and the residue obtained was dissolved in heated ethyl acetate. This solution was allowed to cool, and the solid which had precipitated was taken out by filtration. This recrystallization operation was repeated, and the solid obtained was dried under vacuum to obtain 120 g of 1,1-bis(p-methoxycarbonyloxyphenyl)cyclohexane as a white solid (yield, 84%).

The compound synthesized was subjected to $^1$H-NMR spectroscopy and $^{13}$C-NMR spectroscopy (Avance 400, manufactured by Bruker GmbH: measurement conditions; 400 MHz, CDCl$_3$, TMS) to identify the structure thereof. The results of the analysis are shown below.

$^1$H-NMR (400 MHz, CDCl$_3$) δ 7.26 (2H, d, J=8.8 Hz), 7.43 ppm (2H, d, J=8.8 Hz), 3.88 (6H, s), 2.27-2.22 ppm (4H, m), 1.60-1.45 ppm (6H, m)

$^{13}$C-NMR (100 MHz, CDCl$_3$) δ 154.27 ppm, 148.75 ppm, 145.98 ppm, 128.20 ppm, 120.57 ppm, 55.30 ppm, 45.69 ppm, 37.23 ppm, 26.17 ppm, 22.69 ppm From the results of the analysis by $^1$H-NMR and $^{13}$C-NMR spectroscopy, the compound obtained was ascertained to be 1,1-bis(p-methoxycarbonyloxyphenyl)cyclohexane.

Example B-4

A sheet-form battery was produced and evaluated for overcharge characteristics, output characteristics, and high-temperature storability in the same manners as in Example B-1, except that 1,1-bis(p-methoxycarbonyloxyphenyl)cyclohexane was added in an amount of 1.2% by mass in place of the 2,2-bis(p-methoxycarbonyloxyphenyl)propane in preparing the electrolytic solution of Example B-1. The results of the evaluation are shown in Table 2.

Comparative Example B-1

A sheet-form battery was produced and evaluated for overcharge characteristics, output characteristics, and high-temperature storability in the same manners as in Example B-1, except that the 2,2-bis(p-methoxycarbonyloxyphenyl)propane was omitted in preparing the electrolytic solution of Example B-1. The results of the evaluation are shown in Table 2.

Comparative Example B-2

A sheet-form battery was produced and evaluated for overcharge characteristics, output characteristics, and high-temperature storability in the same manners as in Example B-1, except that cyclohexylbenzene was added in an amount of 2% by mass in place of the 2,2-bis(p-methoxycarbonyloxyphenyl)propane in preparing the electrolytic solution of Example B-1. The results of the evaluation are shown in Table 2.

Comparative Example B-3

A sheet-form battery was produced and evaluated for overcharge characteristics, output characteristics, and high-temperature storability in the same manners as in Example B-1, except that cyclohexylbenzene was added in an amount of 1% by mass in place of the 2,2-bis(p-methoxycarbonyloxyphenyl)propane in preparing the electrolytic solution of Example B-1. The results of the evaluation are shown in Table 2.

Example B-5

A sheet-form battery was produced and evaluated for overcharge characteristics, output characteristics, and high-temperature storability in the same manners as in Example B-1, except that 1,1-bis(p-methoxysulfonyloxyphenyl)cyclohexane was added in an amount of 2.65% by mass in place of the 2,2-bis(p-methoxycarbonyloxyphenyl)propane in preparing the electrolytic solution of Example B-1. The results of the evaluation are shown in Table 2.

Example B-6

A sheet-form battery was produced and evaluated for overcharge characteristics, output characteristics, and high-temperature storability in the same manners as in Example B-1, except that 2,2-bis(p-methoxysulfonyloxyphenyl)propane was added in an amount of 2.4% by mass in place of the 2,2-bis(p-methoxycarbonyloxyphenyl)propane in preparing the electrolytic solution of Example B-1. The results of the evaluation are shown in Table 2.

Comparative Example B-4

A sheet-form battery was produced and evaluated for overcharge characteristics, output characteristics, and high-temperature storability in the same manners as in Example B-1, except that 2,2-diphenylpropane was added in an amount of 1.2% by mass in place of the 2,2-bis(p-methoxycarbonyloxyphenyl)propane in preparing the electrolytic solution of Example B-1. The results of the evaluation are shown in Table 2.

Comparative Example B-5

A sheet-form battery was produced and evaluated for overcharge characteristics, output characteristics, and high-temperature storability in the same manners as in Example B-1, except that 2,2-bis(p-acetoxyphenyl)propane was added in an amount of 2.0% by mass in place of the 2,2-bis(p-methoxycarbonyloxyphenyl)propane in preparing the electrolytic solution of Example B-1. The results of the evaluation are shown in Table 2.

Reference Example B-1

A sheet-form battery was produced and evaluated for overcharge characteristics, output characteristics, and high-temperature storability in the same manners as in Example B-1, except that 1,1-diphenylcyclohexane was added in an amount of 1.5% by mass in place of the 2,2-bis(p-methoxycarbonyloxyphenyl)propane in preparing the electrolytic solution of Example B-1. The results of the evaluation are shown in Table 2.

In Examples B-1 to B-6, Comparative Examples B-1 to B-5, and Reference Example B-1, the addition amount of each compound serving as an additive shown in Table 2 was determined on the basis of the number of phenyl groups present in the compound or of the number of moles of the compound in order that a specific structure within the compound be accurately evaluated as an object to be evaluated.

and characteristics after the high-temperature storage test. The batteries of Comparative Examples A-2 to A-6 and A-8 show a large evolved-gas amount after overcharge and have excellent safety, but have poor characteristics after the high-temperature storage test. Furthermore, Comparative Example A-10 has poor characteristics after the high-temperature storage test, although excellent in terms of initial characteristics.

The batteries of Examples A-1 and A-2 show a large evolved-gas amount after overcharge to have high safety during overcharge, and have excellent characteristics after the high-temperature storage test. It can hence be seen that the batteries employing the nonaqueous electrolytic solutions according to the invention are highly safe during overcharge and have excellent high-temperature continuous-charge characteristics.

Incidentally, a secondary battery is a battery which is used while being repeatedly charged and discharged, and in

TABLE 1

| | Additive 1 | Addition amount wt % | Additive 2 | Addition amount wt % | Initial capacity | Residual capacity after high-temperature storage | Gas amount after overcharge |
|---|---|---|---|---|---|---|---|
| Example A-1 | methyl 3-phenylpropyl carbonate | 2.0 | — | — | 0.99 | 0.99 | 6.0 |
| Comparative Example A-1 | — | — | — | — | 1.00 | 1.00 | 1.0 |
| Comparative Example A-2 | cyclohexylbenzene | 2.0 | — | — | 0.98 | 0.97 | 6.6 |
| Comparative Example A-3 | methyl phenyl carbonate | 2.0 | — | — | 0.97 | 0.97 | 2.9 |
| Comparative Example A-4 | n-butyl carbonate | 2.0 | — | — | 0.99 | 0.95 | 4.6 |
| Comparative Example A-5 | 3-phenylpropyl acetate | 2.0 | — | — | 1.00 | 0.93 | 4.6 |
| Comparative Example A-6 | phenethyl butyrate | 2.0 | — | — | 0.99 | 0.95 | 2.3 |
| Example A-2 | methyl 3-phenylpropyl carbonate | 2.0 | VC | 0.5 | 1.01 | 1.00 | 8.6 |
| Comparative Example A-7 | — | — | VC | 0.5 | 1.00 | 1.01 | 1.4 |
| Comparative Example A-8 | cyclohexylbenzene | 2.0 | VC | 0.5 | 0.99 | 0.98 | 8.6 |
| Comparative Example A-9 | benzyl methyl carbonate | 2.0 | — | — | — | — | 2.1 |
| Comparative Example A-10 | benzyl methyl carbonate | 2.0 | VC | 0.5 | 1.00 | 0.98 | — |

In Table 1, VC represents vinylene carbonate.

In Table 1, the initial capacity, residual capacity after high-temperature storage, and gas amount after overcharge were shown as normalized values with respect to the values of Comparative Example A-1 which were taken as 1.0 or 1.00.

As apparent from Table 1, the batteries of Comparative Examples A-1, A-7, and A-9 show too small an evolved-gas amount after overcharge and have low safety during overcharge, although excellent in terms of initial characteristics which only a slight difference in residual capacity exerts a considerable influence on the continuous-charge performance.

For example, a battery which showed a residual capacity of 0.99 (99%) is compared with a battery which showed a residual capacity of 0.96 (96%). In cases when the two batteries are subjected to 100 cycles of charge/discharge, the resultant charge capacity of the former battery is $0.99^{100} \approx 0.366 = 36.6\%$, whereas that of the latter is $0.96^{100} \approx 0.0168 \approx 1.7\%$. That is, the difference of 3% per cycle results in a difference of 20 times or more through 100 cycles.

It is thus understood that a difference on the order of percent in the residual capacity after high-temperature storage seriously affects the continuous-charge characteristics.

overcharge. Consequently, these batteries are considered to have high safety during overcharge.

A comparison between Examples B-1 to B-4 and Comparative Examples B-2 and B-3 indicates that the batteries of the Examples have a high initial output and a high residual capacity after storage even when the addition amount is

TABLE 2

|  | Additive | Addition amount mass % | Initial | | After storage | | Overcharge characteristics | |
|---|---|---|---|---|---|---|---|---|
|  |  |  | Capacity | Output | Residual capacity | Output | Gas amount | OCV/V |
| Example B-1 | 2,2-bis(p-methoxycarbonyl-oxyphenyl)-propane | 2.2 | 1.00 | 1.00 | 1.01 | 1.01 | 2.90 | 4.65 |
| Example B-2 | 2,2-bis(p-methoxycarbonyl-oxyphenyl)-propane | 1.1 | 1.00 | 1.00 | 1.00 | 1.04 | — | — |
| Example B-3 | 1,1-bis(p-methoxycarbonyl-oxyphenyl)cyclohexane | 2.4 | 1.00 | 1.01 | 1.00 | 0.98 | 4.50 | 4.65 |
| Example B-4 | 1,1-bis(p-methoxycarbonyl-oxyphenyl)cyclohexane | 1.2 | 1.00 | 1.00 | 1.00 | 0.99 | — | — |
| Comparative Example B-1 | none | — | 1.00 | 1.00 | 1.00 | 1.00 | 1.00 | 4.7 |
| Comparative Example B-2 | cyclohexylbenzene | 2.0 | 0.99 | 0.87 | 0.96 | 0.86 | 3.30 | 4.65 |
| Comparative Example B-3 | cyclohexylbenzene | 1.0 | 1.00 | 0.94 | 0.98 | 0.98 | 3.00 | 4.69 |
| Example B-5 | 1,1-bis(p-methoxysulfonyl-oxyphenyl)cyclohexane | 2.65 | 1.00 | 0.95 | 1.01 | 0.96 | 3.63 | 4.62 |
| Example B-6 | 2,2-bis(p-methoxysulfonyl-oxyphenyl)-propane | 2.4 | 1.00 | 0.95 | 1.01 | 0.93 | 3.13 | 4.62 |
| Comparative Example B-4 | 2,2-diphenyl-propane | 1.2 | 1.00 | 0.95 | 1.00 | 0.95 | 1.44 | 4.68 |
| Comparative Example B-5 | 2,2-bis(p-acetoxyphenyl)-propane | 2.0 | 0.99 | 0.89 | 0.98 | 0.75 | 2.56 | 4.69 |
| Reference Example B-1 | 1,1-diphenyl-cyclohexane | 1.5 | 1.00 | 0.94 | 1.00 | 0.93 | 2.56 | 4.66 |

In Table 2, the initial capacity, residual capacity after high-temperature storage, gas amount after overcharge, and output were shown as normalized values with respect to the values of Comparative Example B-1 which were taken as 1.00.

As apparent from Table 2, the batteries of Comparative Examples B-2 and B-3 have a large amount of gas evolved during overcharge and a low OCV after overcharge as compared with the battery of Comparative Example B-1, to which no additive for overcharge has been added, and hence have excellent safety during overcharge. However, as the addition amount increased, not only the initial output of the batteries decreased but also the residual capacity after storage and the output also decreased considerably.

The batteries of Examples B-1 and B-3 compare favorably with Comparative Examples B-2 and B-3 in evolved-gas amount after overcharge and show a low OCV after increased, and compare favorably with Comparative Example B-1, to which no additive for overcharge has been added. It can hence be seen that the batteries employing the nonaqueous electrolytic solutions according to the invention are highly safe during overcharge and have excellent high-temperature storability.

Moreover, Comparative Example B-4 has a small amount of gas evolved during overcharge, and Comparative Example B-5 shows a low output. Meanwhile, Examples B-5 and B-6 show a large amount of gas evolved during overcharge and have a low OCV after overcharge. It can hence be seen that the batteries of the Examples are highly safe during overcharge and can retain both the capacity and the output.

While the invention has been described in detail and with reference to specific embodiments thereof, it will be apparent to one skilled in the art that various changes and modifications can be made therein without departing from the spirit and scope thereof.

This application is based on a Japanese patent application filed on Mar. 30, 2012 (Application No. 2012-82142) and a Japanese patent application filed on Oct. 26, 2012 (Application No. 2012-236679), the contents thereof being incorporated herein by reference.

INDUSTRIAL APPLICABILITY

The nonaqueous-electrolyte battery employing the nonaqueous electrolytic solution of the invention has enhanced safety during overcharge and, despite this, has high capacity and excellent high-temperature continuous-charge characteristics. This battery can hence be used in various known applications.

Specific examples thereof include notebook type personal computers, pen-input personal computers, mobile personal computers, electronic-book players, portable telephones, portable facsimile telegraphs, portable copiers, portable printers, headphone stereos, video movie cameras, liquid-crystal TVs, handy cleaners, portable CD players, mini-disk players, transceivers, electronic pocketbooks, electronic calculators, memory cards, portable tape recorders, radios, backup power sources, motors, motor vehicles, motor cycles, bicycles fitted with a motor, bicycles, illuminators, toys, game machines, clocks and watches, power tools, stroboscopes, cameras, power sources for load leveling, and power sources for storing natural energy. This battery can be used in all applications ranging from small-size applications to large-size applications.

The invention claimed is:

1. A nonaqueous electrolytic solution, comprising:
   an electrolyte;
   a nonaqueous solvent; and
   at least one of a compound represented by formula (I) and a compound represented by formula (II):

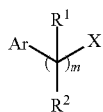

(I)

-continued

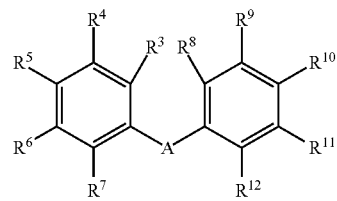

(II)

wherein, in formula (I), Ar represents a phenyl group, m represents an integer of 2 or larger, X represents an alkoxycarbonyloxy group, an organic sulfonate group, or a phosphoric acid ester group, and $R^1$ and $R^2$ each independently represent a hydrogen atom, a halogen atom, or an optionally substituted hydrocarbon group having 1-12 carbon atoms, and wherein, in formula (II), A represents an optionally substituted alkylidene groups or cycloalkylidene groups, $R^3$ to $R^{12}$ each independently represent a hydrogen atom, a halogen atom, an optionally substituted hydrocarbon group having 1-12 carbon atoms, an alkoxy group, an alkoxycarbonyloxy group, an organic sulfonate group, or a phosphoric acid ester group, and at least one of the $R^3$ to $R^{12}$ representing an alkoxycarbonyloxy group, an organic sulfonate group, or a phosphoric acid ester group.

2. The nonaqueous electrolytic solution according to claim 1, wherein $R^1$ and $R^2$ in formula (I) are each a hydrogen atom.

3. The nonaqueous electrolytic solution according to claim 1, wherein the total content of the compound represented by formula (I) and the compound represented by formula (II) in the nonaqueous electrolytic solution is 0.001-10% by mass.

4. The nonaqueous electrolytic solution according to claim 1, further comprising:
   at least one compound selected from the group consisting of cyclic carbonate compounds having a carbon-carbon unsaturated bond, cyclic carbonate compounds having a fluorine atom, monofluorophosphoric acid salts, and difluorophosphoric acid salts.

5. A nonaqueous-electrolyte battery comprising: a negative electrode and a positive electrode which are capable of occluding and releasing lithium ions; and a nonaqueous electrolytic solution, wherein the nonaqueous electrolytic solution is the nonaqueous electrolytic solution according to claim 1.

6. The nonaqueous electrolytic solution according to claim 1, comprising the compound of formula (I).

7. The nonaqueous electrolytic solution according to claim 1, comprising the compound of formula (II).

* * * * *